United States Patent
Stoner et al.

(10) Patent No.: US 6,437,106 B1
(45) Date of Patent: Aug. 20, 2002

(54) PROCESS FOR PREPARING 6-O-SUBSTITUTED ERYTHROMYCIN DERIVATIVES

(75) Inventors: Eric J. Stoner, Kenosha, WI (US); Matthew J. Peterson, Gurnee, IL (US); Yi-Yin Ku, Buffalo Grove, IL (US); Russell D. Cink, Grayslake, IL (US); Arthur J. Cooper, Lake Villa, IL (US); Mahendra N. Deshpande, Gurnee, IL (US); Tim Grieme, Chicago, IL (US); Anthony R. Haight, Wadsworth, IL (US); David R. Hill, Gurnee, IL (US); Margaret Chi-Ping Hsu, Vernon Hills, IL (US); Steven A. King, Gurnee, IL (US); Marvin Robert Leanna, Grayslake, IL (US); Elaine C. Lee, Mundelein, IL (US); Maureen A. McLaughlin, Evanston, IL (US); Howard E. Morton, Gurnee, IL (US); James J. Napier, Antioch, IL (US); Daniel J. Plata, Wadsworth, IL (US); Prasad S. Raje, Lindenhurst, IL (US); Michael Rasmussen; David Riley, both of Kenosha, WI (US); Jien-Heh J. Tien, Vernon Hills, IL (US); Steven J. Wittenberger, Mundelein, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/518,281

(22) Filed: Mar. 3, 2000

Related U.S. Application Data

(60) Provisional application No. 60/140,968, filed on Jun. 24, 1999.

(51) Int. Cl.$^7$ .................................................. C07H 1/00
(52) U.S. Cl. ......................... 536/7.4; 536/7.2; 536/18.5
(58) Field of Search ........................... 536/7.2, 7.4, 18.5

(56) References Cited

U.S. PATENT DOCUMENTS

| | | |
|---|---|---|
| 3,780,020 A | 12/1973 | Evans |
| 4,331,803 A | 5/1982 | Watanabe et al. |
| 4,668,776 A | 5/1987 | Yamada et al. |
| 4,670,549 A | 6/1987 | Morimoto et al. |
| 4,672,109 A | 6/1987 | Watanabe et al. |
| 4,680,386 A | 7/1987 | Morimoto et al. |
| 4,990,602 A | 2/1991 | Morimoto et al. |
| 5,274,085 A | 12/1993 | Amano et al. |
| 5,719,272 A | 2/1998 | Yang et al. |
| 5,808,017 A | 9/1998 | Chang |
| 5,837,829 A | 11/1998 | Ku |
| 5,852,180 A | 12/1998 | Patel |
| 5,864,023 A | 1/1999 | Ku et al. |
| 5,866,549 A | 2/1999 | Or et al. |
| 5,872,229 A | 2/1999 | Liu et al. |
| 5,892,008 A | 4/1999 | Ku et al. |
| 5,929,219 A | 7/1999 | Hill |

FOREIGN PATENT DOCUMENTS

| | | |
|---|---|---|
| DE | 1966310 | 8/1969 |
| EP | 0260938 | 9/1987 |
| WO | 97 42206 A | 11/1997 |
| WO | 98 09978 A | 3/1998 |
| WO | 99 11651 A | 3/1999 |
| WO | 99 16779 A | 4/1999 |
| WO | 99 21864 A | 5/1999 |

OTHER PUBLICATIONS

C. Goux, Synlett, vol. 723 (1990).
Lakhmiri, Synthetic Communications, vol. 20 (10), pp. 1551–1554 (1990).
Lakhmiri, Tetrahedron Letters, vol. 30 (35), pp. 4673–4676 (1989).
Lakhmiri, J. Carbohydrate Chemistry, vol. 12 (2), p. 223 (1993).
L. Cotarca, Synthesis, p. 553.
Beller, Angew Chem. Int. Ed. Engl., vol. 34 (17), p. 1848 (1995).
Sigal, J. Am. Chem. Soc., vol. 78, pp. 388–395 (1956).
Baker, J. Org. Chem., vol. 53, p. 2340 (1988).
Houlihan, Can. J. Chem., p. 153 (1985).
Green and Wuts, Protective Groups In Organic Synthesis, 3$^{rd}$ edition, John Wiley & Sons, New York (1999).
Berge, et al. J. Pharmaceutical Sciences, 66: 1–19 (1977).
Roche, ed., Bioreversible Carriers In Drug Design, American Pharmaceutical Association and Pergamon Press, 1987.

*Primary Examiner*—Elli Peselev
(74) *Attorney, Agent, or Firm*—B. Gregory Donner

(57) ABSTRACT

In one aspect, the invention relates to a process for preparing 6-O-substituted erythromycin derivatives comprising reacting 2'-substituted and optionally 4"-substituted 9-oxime erythromycin derivatives with an alkylating agent in the presence of a palladium catalyst and phosphine. In another aspect, the invention relates to processes for preparing 6-O-substituted erythromycin ketolides using the palladium-catalyzed alkylation reaction.

30 Claims, No Drawings

PROCESS FOR PREPARING 6-O-SUBSTITUTED ERYTHROMYCIN DERIVATIVES

This application claims priority from the U.S. Provisional Application Serial No. 60/140,968, filed on Jun. 24, 1999.

TECHNICAL FIELD

The present invention relates to a process for preparing 6-O-substituted erythromycin derivatives and 6-O-substituted erythromycin ketolides thereof. Specifically, the invention relates to a palladium-catalyzed process for preparing 6-O-substituted erythromycin derivatives from erythromycins using alkylating agents in presence of a phosphine and their subsequent conversion into 6-O-substituted erythromycin ketolides.

BACKGROUND OF THE INVENTION

6-O-Methylerythromycin A (clarithromycin) is a potent macrolide antibiotic disclosed in U.S. Pat. No. 4,331,803.

The process for making clarithromycin, in general, can be thought of as a four-step procedure beginning with erythromycin A as the starting material:

Step 1: optionally convert the 9-oxo group to an oxime;
Step 2: protect the 2' and 4" hydroxyl groups;
Step 3: methylate the 6-hydroxyl group; and
Step 4: deprotect at the 2', 4" and 9-positions.

A variety of means for preparing 6-O-methylerythromycin A have been described in the literature. 6-O-Methylerythromycin A can be prepared by methylating a 2'-O-3'-N-dibenzyloxycarbonyl-des-N-methyl derivative of erythromycin A (U.S. Pat. No. 4,331,803). 6-O-Methylerythromycin A can also be made from 9-oxime erythromycin A derivatives (See, e.g., U.S. Pat. Nos. 5,274,085; 4,680,386; 4,668,776; 4,670,549 and 4,672,109, 4,990,602 and European Patent Application 0260938 A2). Several commonly-owned U.S. Pat. Nos. 5,872,229; 5,719,272; 5,852,180; 5,864,023; 5,808,017; 5,837,829 and 5,929,219 disclose the use of alternate protecting groups for the oxime hydroxyl, and the 2'- and 4"-hydroxyls in the process of making the 6-O-methyl erythromycin derivatives.

Since the discovery of clarithromycin, new macrolide antibiotic compounds have been discovered. New classes of particularly effective macrolide antibiotics are disclosed in U.S. Pat. No. 5,866,549. The 6-O-position of the macrolide core can be substituted with a $C_2$–$C_6$ alkenyl group. Such compounds generally have been prepared by the processes described for the preparation of 6-O-methylerythromycin A. However, the substitution at the 6-O-position with substituents other than the methyl group is not easy to accomplish and is accompanied by side reactions, by-products and low yields.

Therefore, there is considerable effort directed towards discovering more efficient and cleaner methods of introducing substituents other than the methyl in the 6-position of the erythromycin derivatives.

Palladium-catalyzed allylation of alcohol hydroxyl groups is known in the literature. See for example, Lakhmiri et al., "Synthesis De O-glycosides D'Alcenyles", *J. Carbohydrate Chemistry,* 12(2), 223, (1993); Lakhmiri et al., *Tetrahedron Letters,* 30(35), No. 35, pp 4673–4676, (1989); and Lakhmiri et al., "An Improved Synthesis of Allyl Ethers of Carbohydrates", *Synthetic Communications,* 20 (10), 1551–1554 (1990). Palladium-catalyzed allylation of phenol derivatives using allyl t-butyl carbonate is disclosed in Goux C. et al., *Synlett.,* 725 (1990). However, there are no known reports of palladium-catalyzed substitution, derivatization or selective allylation of hydroxyl groups of erythromycin derivatives.

SUMMARY OF THE INVENTION

In one aspect, therefore, the present invention relates to a process for preparing 6-O-substituted erythromycin derivatives comprising reacting an erythromycin derivative with an alkylating agent having the formula:

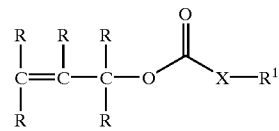

wherein

R is independently selected from the group consisting of: hydrogen, an alkyl group of one to ten carbon atoms, halogen, aryl, substituted aryl, heteroaryl and substituted heteroaryl at each occurrence;

$R^1$ is an alkyl group of one to ten carbon atoms, and X is O or NR', wherein R' is alkyl or aryl, or $R^1$ and R' taken together form an aromatic or non-aromatic ring;

in the presence of a palladium catalyst and a phosphine.

The erythromycin derivative used in the process of the invention is represented by formula (1) below:

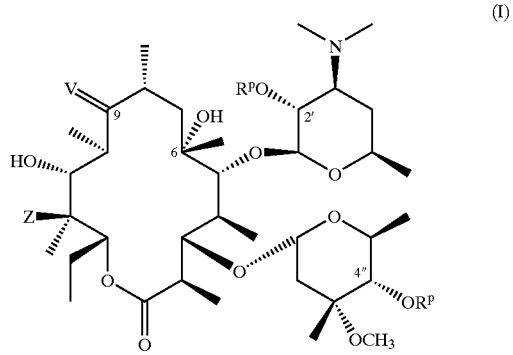

(I)

wherein:

$R^P$ is independently a hydrogen or a hydroxyl-protecting group at each ocurrence except that $R^P$ may not simultaneously be hydrogen at both positions;

V is selected from the group consisting of:
a) O
b) an oxime having the formula N—O—$R^2$; wherein $R^2$ is selected from the group consisting of:
hydrogen,
a loweralkenyl group,
an aryl(loweralkyl) group, and
a substituted aryl(loweralkyl) group;
c) an oxime having the formula

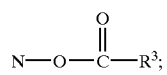

wherein
R³ is selected from the group consisting of:
alkyl,
alkylaryl,
aryl, and
substituted aryl;
d) an oxime having the formula

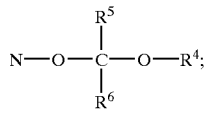

wherein
R⁴ is selected from the group consisting of:
a loweralkyl group,
a cycloalkyl group,
a phenyl group, and
an aryl(loweralkyl) group;
or R and R⁵ or R⁴ and R⁶ and the atoms to which they are attached are taken together form a 5- to 7-membered ring containing one oxygen atom; and
R⁵ and R⁶ are independently selected from the group consisting of:
a hydrogen atom,
a loweralkyl group,
a phenyl group,
an aryl(loweralkyl) group;
or any pair of substituents selected from (R⁴ and R⁵), (R⁴ and R⁶) or (R⁵ and R⁶) and the atoms to which they are attached are taken together to form a 5- to 7-membered ring optionally containing one oxygen atom; provided that only one pair of substituents (R⁴ and R⁵), (R⁴ and R⁶) or (R⁵ and R⁶) may be taken together with the atoms to which they are attached to form a ring as defined above;
e) an oxime having the formula:

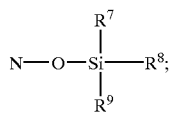

wherein R⁷, R⁸, and R⁹ are independently selected at each occurrence from hydrogen, loweralkyl, aryl-substituted alkyl, aryl, cycloalkyl, and loweralkenyl;
f)

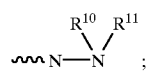

wherein R¹⁰ and R¹¹ are independently selected at each occurrence from hydrogen, alkyl, or nitrogen-protecting group, or R¹⁰ and R¹¹ taken together form a 5- to 7-membered cycloalkyl ring; and
g)

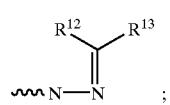

wherein R¹² and R¹³ are independently selected at each occurrence from hydrogen, alkyl or a nitrogen-protecting group; or R¹² and R¹³ taken together form a 5- to 7-membered cycloalkyl ring; and Z is hydroxyl or a protected hydroxyl group.
The 6-O-substituted erythromycin derivative is represented by formula (II)

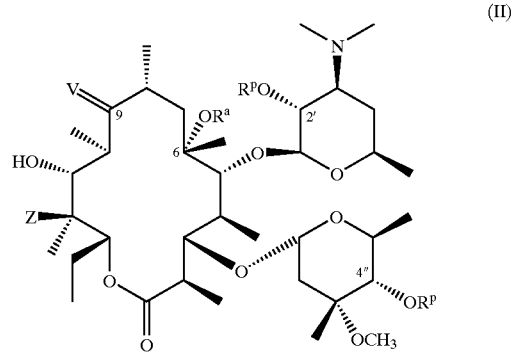

wherein $R^a$ is represented by the formula:

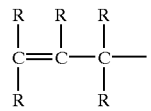

and wherein R, $R^p$, V and Z are as defined above.
The compounds of formula (II) may be optionally deprotected and deoximated to obtain compounds of formula (III)

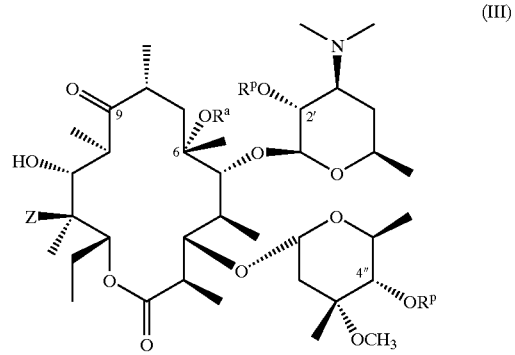

wherein $R^p$, $R^a$ and Z are as defined above.
The compounds of formulas (I), (II) and (III) are useful intermediates in the synthesis of macrolide antibiotics as described in the U.S. Pat. No. 5,866,549, issued Feb. 2, 1999, represented by formula (IV)

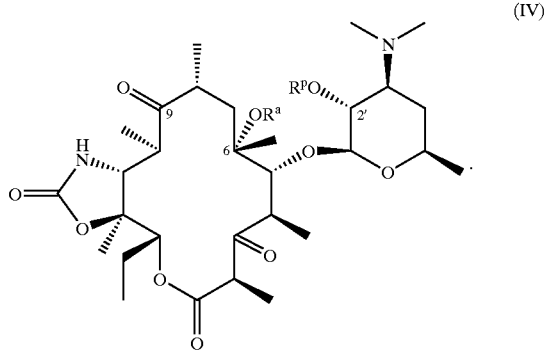

Therefore, in another aspect, the process of invention further comprises the steps of:

(a) reacting the compound of formula (III)

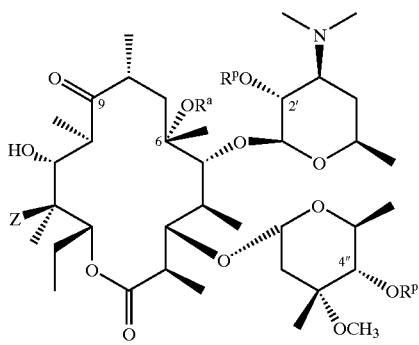

with 1,1'-carbonyldiimidazole in the presence of an amine base or an amine base catalyst followed by a reaction with ammonia or ammonium hydroxide optionally carried out in the presence of a strong base to give a compound having the formula:

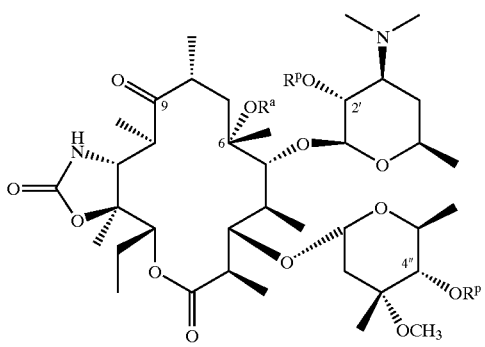

(b) removing the cladinose moiety from the compound obtained in step (a) by hydrolysis with acid to give a compound having the formula:

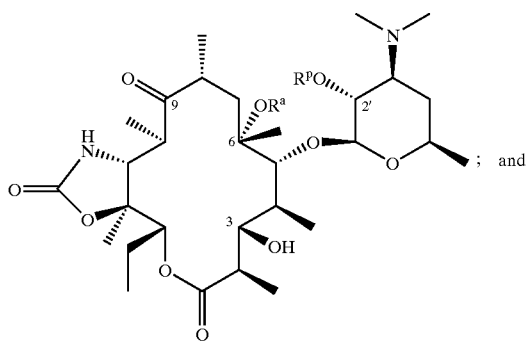

; and (c) oxidizing the 3-hydroxyl group, and optionally deprotecting and isolating the desired compound.

In yet another aspect, the present invention relates to the process for preparing a compound of formula (IV) by removing the cladinose moiety of a compound of formula (I') with acid; protecting the 2'- and optionally the 3-hydroxyl functionalities; alkylating the compound obtained therefrom with an alkylating agent; deoximating; preparing an 11,12-cyclic carbamate; deprotecting the 3-hydroxyl, if protected; oxidizing the 3-hydroxyl group; and optionally deprotecting the 2'-hydroxyl to afford a compound of formula (IV). The process of the invention is an efficient process and provides higher yields of the desired compounds compared with known alkylation processes.

DETAILED DESCRIPTION OF THE INVENTION

Definitions

A number of terms are used herein to designate particular elements of the present invention. When so used, the following meanings are intended:

The term "erythromycin derivative" refers to erythromycins having a 9-keto group or wherein the 9-keto group is converted into an oxime having no substituents or specified substituents in place of the oxime hydroxyl hydrogen and optionally having conventional protecting groups in place of the hydrogen of the 2' and 4" hydroxyl groups.

The term "erythromycin 9-oxime derivative" as used herein refers to erythromycins wherein the 9-keto group is converted into an oxime as described above.

The term "6-O-substituted erythromycin derivatives" as used herein refers to erythromycin 9-oxime derivatives or erythromycins having the hydrogen of the 6-hydroxyl group substituted with various substituents.

The term "hydroxyl-protecting group" is well-known in the art and refers to substituents on functional hydroxyl groups of compounds undergoing chemical transformation which prevent undesired reactions and degradations during a synthesis (see, for example, T. H. Greene and P. G. M. Wuts, Protective Groups in Organic Synthesis, 3rd edition, John Wiley & Sons, New York (1999)). Examples of hydroxyl-protecting groups include, but are not limited to, benzoyl, benzyloxycarbonyl, acetyl, or a substituted silyl group of formula $SiR^7R^8R^9$, wherein $R^7$, $R^8$ and $R^9$ are the same or different and each is a hydrogen atom, a loweralkyl group, an aryl-substituted alkyl group in which the alkyl moiety has 1 to 3 carbon atoms, an aryl group, a cycloalkyl group having 5 to 7 carbon atoms, or a loweralkenyl group having 2 to 5 carbon atoms and wherein at least one of $R^7$, $R^8$ and $R^9$ is not a hydrogen atom; and the like.

The term "alkyl" or "loweralkyl" refers to an alkyl radical containing one to six carbon atoms including, but not limited to, methyl, ethyl, propyl, isopropyl, n-butyl, t-butyl and neopentyl.

The term "loweralkoxy" refers to a loweralkyl group as previously defined attached to a parent molecular moiety by an ether linkage.

The term "loweralkoxy(methyl)" refers to an alkoxy group as described above attached to a parent molecular moiety via a methylene group (—$CH_2$—).

The term "protected hydroxyl" refers to a hydroxyl group protected with a hydroxyl protecting group, as defined above.

The term "polar aprotic solvent" refers to polar organic solvents lacking an easily removed proton, including, but not limited to, N,N-dimethylformamide, dimethyl sulfoxide, N-methyl-2-pyrrolidone, hexamethylphosphoric triamide, tetrahydrofuran, 1,2-dimethoxyethane, 1,2-dichloroethane, acetonitrile or ethyl acetate, and the like or a mixture thereof.

The term "aryl" as used herein refers to a mono- or bicyclic carbocyclic ring system having one or two aromatic rings including, but not limited to, phenyl, naphthyl, tetrahydronaphthyl, indanyl, indenyl and the like. Aryl groups (including bicyclic aryl groups) can be unsubstituted or substituted with one, two or three substituents independently selected from loweralkyl, substituted loweralkyl, haloalkyl, alkoxy, thioalkoxy, amino, alkylamino, dialkylamino, acylamino, benzyloxycarbonyl, cyano, hydroxyl, halo, mercapto, nitro, carboxaldehyde, carboxy, alkoxycarbonyl, carboxamide, and protected hydroxyl. In addition, substituted aryl groups include tetrafluorophenyl and pentafluorophenyl.

The term "heteroaryl", as used herein, refers to a mono- or bicyclic fused aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

The term "substituted aryl" as used herein refers to an aryl group as defined herein substituted by independent replacement of one, two or three of the hydrogen atoms thereon with Cl, Br, F, I, OH, CN, $C_1$–$C_3$-alkyl, $C_1$–$C_6$-alkoxy, $C_1$–$C_6$-alkoxy substituted with aryl, haloalkyl, thioalkoxy, amino, alkylamino, dialkylamino, mercapto, nitro, carboxaldehyde, carboxy, alkoxycarbonyl and carboxamide. In addition, any one substituent may be an aryl, heteroaryl, or heterocycloalkyl group. Also, substituted aryl groups include tetrafluorophenyl and pentafluorophenyl.

The term "substituted heteroaryl" as used herein refers to a heteroaryl group as defined herein substituted by independent replacement of one, two or three of the hydrogen atoms thereon with Cl, Br, F, I, OH, CN, $C_1$–$C_3$-alkyl, $C_1$–$C_6$-alkoxy, $C_1$–$C_6$-alkoxy substituted with aryl, haloalkyl, thioalkoxy, amino, alkylamino, dialkylamino, mercapto, nitro, carboxaldehyde, carboxy, alkoxycarbonyl and carboxamide. In addition, any one substituent may be an aryl, heteroaryl, or heterocycloalkyl group.

The term "pharmaceutically acceptable salts" as used herein refers to those carboxylate salts, esters, and prodrugs of the compound of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention.

Pharmaceutically acceptable salts are well known in the art and refer to the relatively non-toxic, inorganic and organic acid addition salts of the compound of the present invention. For example, S. M. Berge, et al. describe pharmaceutically acceptable salts in detail in *J. Pharmaceutical Sciences*, 66: 1–19 (1977) which is incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters includes formates, acetates, propionates, butyrates, acrylates and ethylsuccinates.

The term "pharmaceutically acceptable solvate" represents an aggregate that comprises one or more molecules of the solute, such as a compound of the invention, with one or more molecules of solvent.

The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, *Pro-drugs as Novel Delivery Systems*, Vol. 14 of the A.C.S. Symposium Series, and in Edward B. Roche, ed., *Bioreversible Carriers in Drug Design*, American Pharmaceutical Association and Pergamon Press, 1987, both of which are incorporated herein by reference.

A process of the invention involves preparing a compound of formula (IV) by reacting a compound of formula (I) with a suitable alkylating agent to obtain a compound of formula (II), and carrying out the subsequent transformations as previously described in steps (a)–(c) above. The process of the invention is illustrated in Scheme 1 below.

Scheme 1

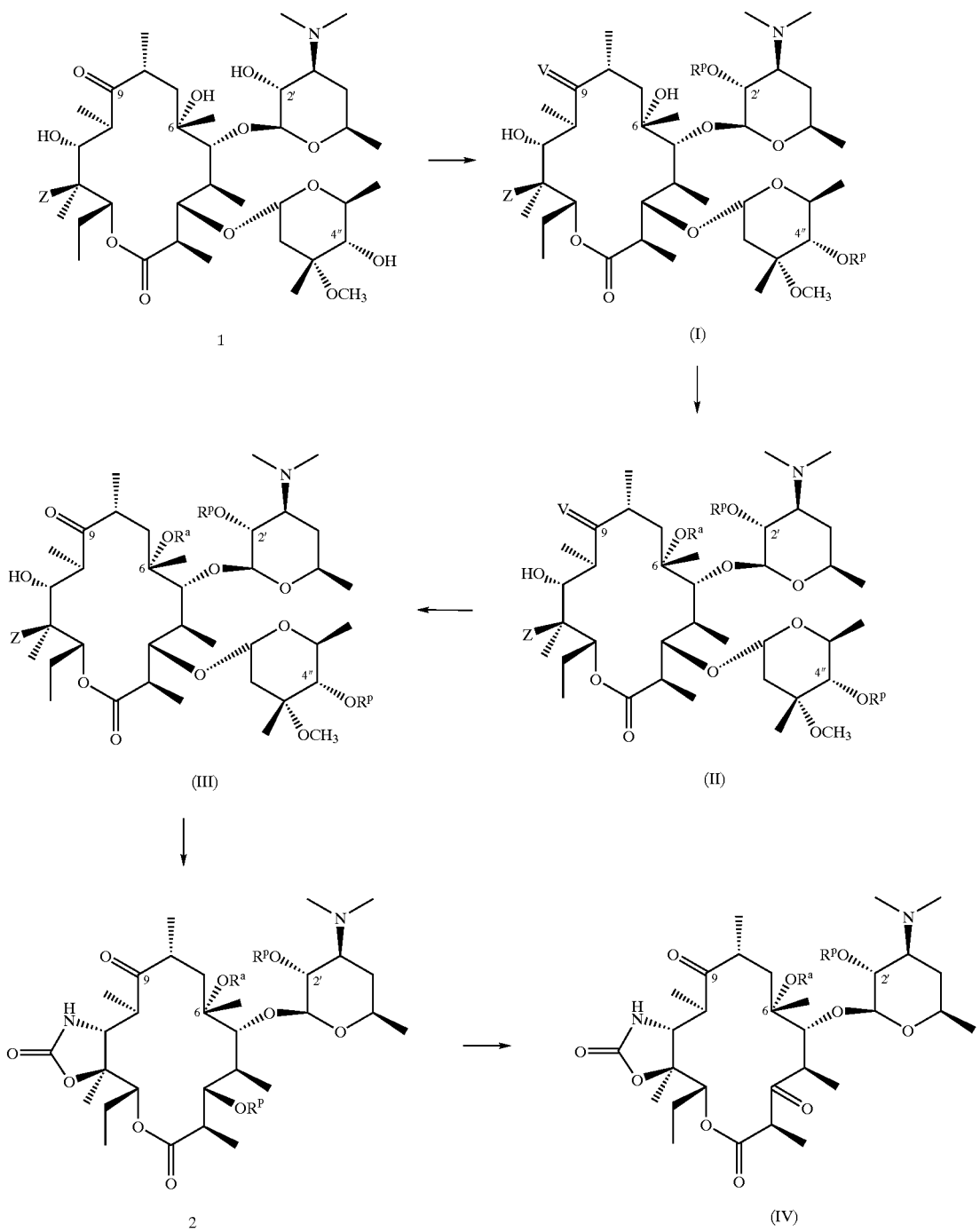

In accordance with Scheme 1, the 9-keto group of erythromycins of formula 1 can be initially converted into an oxime by methods described in U.S. Pat. No. 4,990,602, followed by the protection of the 2'- and optionally protecting the 4"-hydroxyl groups of the erythromycin derivatives to obtain erythromycin 9-oxime of formula (1).

The preparation of protected erythromycins is also described in the U.S. Pat. Nos. 4,990,602; 4,331,803; 4,680,386; and 4,670,549 which are incorporated herein by reference. Also incorporated by reference is European Patent Application EP 260,938.

The C-9-carbonyl group of erythromycin can be protected as an oxime represented by V having the formula N—O—$R^2$,

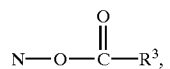

N—O—C($R^5$)($R^6$)—O—$R^4$, or

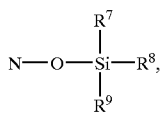

wherein $R^2$, $R^3$, $R^4$, $R^5$, $R^6$, $R^7$, $R^8$ and $R^9$ are as defined above. Preferred oximes are those wherein V is O-(1-isopropoxycyclohexylketal) oxime, and O-benzoyloxime.

Silyl ethers are also particularly useful for protecting the 2'- and the 4"-hydroxyl groups of erythromycin derivatives. The use of silyl ether groups to protect a 9-oxime moiety and the 2'- and 4"-hydroxyl groups is described in U.S. Pat. No. 5,892,008.

The 9-carbonyl group of the erythromycins may also be protected by converting it into erythromycin 9-hydrazone as described in U.S. application Ser. No. 08/927,057 filed Sep. 10, 1997, which issued as U.S. Pat. No. 5,929,219 on Jul. 27, 1999.

The methods of preparing hydrazones are described in Sigal et al., *J. Am. Chem. Soc.,* 78, 388–395, (1956). As for example, the 9-hydrazone is prepared by heating erythromycin at reflux in an alcoholic solvent such as methanol, ethanol or isopropanol in the presence of hydrazine until no starting material remains. The reaction typically lasts from about 12 to 36 hours. The solvent is then removed and the crude solid so obtained is used without further purification.

The amino nitrogen of the 9-hydrazone erythromycin derivative may optionally be protected by the nitrogen protecting groups by the methods described in T. H. Greene and P. G. M. Wuts, Protective Groups in Organic Synthesis, 3rd edition, John Wiley & Sons, New York, Chapter 7, (1999); and P. J. Kocienski, Protective Groups, Thieme, Chapter 6, (1994); and the references cited therein.

As for example, the amino nitrogen of the 9-hydrazone is protected by treating erythromycin 9-hydrazone with 1–2 equivalents of a silylating agent such as triisopropylsilyl triflate in the presence of an organic base such as triethylamine in an aprotic solvent. Preferably, the reaction is carried out in the presence of triethylamine in dichloroethane. The reaction results in the formation of 9-(N-triisopropylsilyl) hydrazone erythromycin derivative which can be protected at the 2'- and optionally at the 4"-positions.

The erythromycin 9-hydrazone derivative may also be converted into an azine by the methods described in, for example, U.S. Pat. No. 3,780,020 and German Patent 1,966,310. As for example, the azine derivative is prepared by treating the hydrazone with an appropriate ketone, aldehyde or an acetal thereof or an orthoformate with or without a co-solvent and either with or without an added dehydrating agent such as molecular sieves. The reaction is carried out at a temperature between room temperature and the boiling point of the ketone, aldehyde, or the co-solvent. The reaction is carried out for about one hour to about 24 hours. The azine nitrogen may be further protected by treating the 9-azine erythromycin derivative with an appropriate ketal in the presence of catalytic quantity of acid such as formic or acetic acid. The reaction mixture is stirred at ambient temperature overnight for 6 to 18 hours. The mixture is then adjusted with base to pH 8–13 and the product extracted into an appropriate solvent.

The 2'- and 4"-hydroxyl groups are protected by reaction with a suitable hydroxyl protecting reagent in an aprotic solvent. Typical hydroxyl-protecting reagents include, but are not limited to, acetylating agents, silylating agents, acid anhydrides, and the like. Examples of hydroxyl protecting reagents are, for example, acetyl chloride, acetic anhydride, benzoyl chloride, benzoic anhydride, benzyl chloroformate, hexamethyldisilazane, and trialkylsilyl chlorides.

Examples of aprotic solvents are dichloromethane, chloroform, tetrahydrofuran (THF), N-methyl pyrrolidinone, dimethylsulfoxide, diethylsulfoxide, N,N-dimethylformamide (DMF), N,N-dimethylacetamide, hexamethylphosphoric triamide, a mixture thereof or a mixture of one of these solvents with ether, tetrahydrofuran, 1,2-dimethoxyethane, 1,2-dichloroethane, acetonitrile, ethyl acetate, acetone and the like. Aprotic solvents do not adversely affect the reaction. Preferably, the solvent is selected from dichloromethane, chloroform, N,N-dimethylformamide, tetrahydrofuran, N-methyl pyrrolidinone or a mixture thereof. A more thorough discussion of solvents and conditions for protecting the hydroxy group can be found in T. W. Greene and P. G. M. Wuts in *Protective Groups in Organic Synthesis,* 3rd ed., John Wiley & Son, Inc., 1999, which is incorporated by reference.

Protection of 2'- and 4"-hydroxyl groups of compound 1 may be accomplished sequentially or simultaneously to provide compound (I), wherein $R^p$ can be, for example, acetyl, benzoyl, trimethylsilyl, and the like. Preferred protecting groups include acetyl, benzoyl, and trimethylsilyl. A particularly preferred group for protecting the hydroxyl and the oxime moieties is the benzoate protecting group, wherein $R^p$ is benzoyl.

Benzoylation of the hydroxyl group is typically accomplished by treating the erythromycin 9-oxime derivative with a benzoylating reagent, for example a benzoyl halide and benzoyl anhydride. A preferred benzoyl halide is benzoyl chloride. Typically, the reaction is accomplished with a benzoic anhydride, which affords the protected erythromycin 9-oxime derivative. Benzoic anhydride is a relatively expensive reagent for the protection of the erythromycin 9-oxime compound.

Alternatively, the erythromycin 9-oxime derivative can be treated with sodium benzoate and benzoyl chloride to afford the protected erythromycin 9-oxime compound. The reagent combination is a more cost-effective alternative to using benzoic anhydride. By generating benzoic anhydride in situ, the reaction allows for the efficient, effective hydroxylation of the 2'- and the 4"-protecting groups and the 9-oxime by using cheaper and more readily available starting materials. Generally, from about 3 to about 4.5 molar equivalents of benzoyl chloride and sodium benzoate are used for each equivalent of erythromycin A 9-oxime. The preferred reaction is carried out using about a 1:1 molar ratio of benzoyl chloride and sodium benzoate. Preferably, the reaction is carried out in tetrahydrofuran as the solvent, optionally in the presence of a base, for example triethylamine or imidazole.

Typically, the erythromycin derivative is isolated after oximation and before treatment with the suitable protecting group. However, the conversion of the erythromycin A with hydroxylamine and formic acid in a methanolic solvent affords an erythromycin A 9-oxime derivative that can be directly converted to the protected erythromycin A 9-oxime derivative without isolation. The preferred amount of hydroxylamine is from about 7 to about 10 molar equivalents relative to the erythromycin A. From about 2 to about 5 moles of formic acid are used for each mole of the erythromycin A starting material.

For the unisolated erythromycin A 9-oxime intermediate, it is preferred that the benzoylation is carried out with benzoic anhydride reagent, optionally in the presence of base. The reaction can be carried out in tetrahydrofuran optionally in a mixture with isopropyl acetate to afford the protected erythromycin A 9-oxime intermediate compound.

The erythromycin derivative of formula (I) is then reacted with an alkylating agent of the formula:

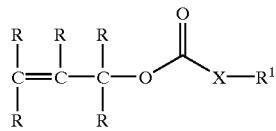

wherein R, $R^1$, and X are as defined above,
in the presence of a palladium catalyst and a phosphine promoter to obtain the compound represented by formula (II)

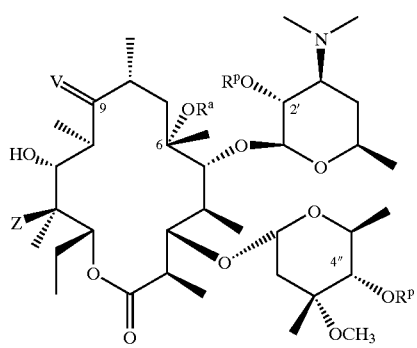

wherein $R^a$, $R^p$, V and Z are as defined above.

Most palladium(0) catalysts are expected to work in this process. Some palladium(II) catalysts, such as palladium(II) acetate, which is converted into a palladium(0) species in-situ by the actions of a phosphine, will work as well. See, for example, Beller et. al. *Angew Chem. Int. Ed. Engl.*, 1995, 34 (17), 1848. The palladium catalyst can be selected from, but is not limited to, the group consisting of palladium(II) acetate, tetrakis(triphenylphosphine)palladium(0), tris (dibenzylideneacetone)dipalladium, (tetradibenzylideneacetone)dipalladium and the like. Palladium on carbon and palladium(II) halide catalysts are less preferred than other palladium catalysts for this process.

The ratio of palladium catalyst to the phosphine generally ranges from about 2:1 to about 1:8.

Suitable phosphines include, but are not limited to, triphenylphosphine, bis(diphenylphosphine)methane, bis(diphenylphosphine)ethane, bis(diphenylphosphine)propane, 1,4-bis(diphenylphosphine)butane, bis(diphenylphosphine)pentane, and tri(o-tolyl)phosphine, and the like.

The reaction is carried out in an aprotic solvent, preferably at elevated temperature, preferably at or above 50 ° C. The aprotic solvent includes, but is not limited to, N,N-dimethylformamide, dimethyl sulfoxide, N-methyl-2-pyrrolidone, hexamethylphosphoric triamide, tetrahydrofuran, 1,2-dimethoxyethane, methyl-t-butyl ether (MTBE), heptane, acetonitrile, isopropyl acetate and ethyl acetate. The most preferred solvents are tetrahydrofuran or toluene.

The alkylating agents useful in the process of the invention are carbonates and carbamates of allylic hydrocarbons, for example allyl carbonates and allyl carbamates. Generally, the alkylating agents useful for the reaction generally have the formula previously described wherein $R^1$ is from about 1 to 10 carbon atoms. The preferred alkylating agents are those wherein $R^1$ is t-butyl group, isopropyl or N,N-diisopropyl, for example, t-butyl carbonate, isopropyl carbonate or N,N-diisopropyl carbamate compounds. Alkylating agents can include, for example, allyl iso-propyl carbonate, allyl t-butyl carbonate, allyl N,N-diisopropyl carbamate, 3-(3-quinolyl)-2-propen-1-ol t-butyl carbonate, and 1-(3-quinolyl)-2-propene-1-ol t-butyl carbonate. The alkylating reagents are obtained by reaction of an alcohol with a wide variety of compounds for incorporating the carbonate or carbamate moiety. The compounds include, but are not limited to, t-butyl chloroformate, 2-(t-butoxycarbonyl-oxyimino)-2-phenyl-acetonitrile, N-t-butoxycarbonyloxy succinimide, di-t-butyl dicarbonate, and 1-(t-butoxy-carbonyl)imidazole and the reaction is carried out in the presence of an organic or an inorganic base. The temperature of the reaction varies from about −30° C. to about 30° C. Preferably, the alkylating reagent is di-t-butyl dicarbonate.

An alternate method of converting the alcohol into the carbonate or carbamate involves treating the alcohol with phosgene or triphosgene to prepare the chloroformate derivative of the alcohol. The chloroformate derivative is then converted into the carbonate or carbamate by the methods described in Cotarca, L., Delogu, P., Nardelli, A., Sunijic, V. *Synthesis*, 1996, 553. The reaction can be carried out in a variety of organic solvents such as dichloromethane, toluene, diethyl ether, ethyl acetate and chloroform in the presence of a base. Examples of bases include, but are not limited to, sodium hydroxide, potassium hydroxide, ammonium hydroxide, sodium carbonate, potassium carbonate, ammonium carbonate, dimethylaminopyridine, pyridine, triethylamine and the like. A wide variety of phase transfer reagents can be used, including tetrabutylammonium halide and the like. The temperature conditions can vary anywhere from 0° C. to about 60° C. The reaction typically takes about 3 to 5 hours to run to completion.

One example of a method for preparing the alkylating agent is described in the commonly owned, U.S. Application Serial No. 60/141,042, filed on Jun. 24, 1999, and is illustrated in Scheme 2 below.

Scheme 2

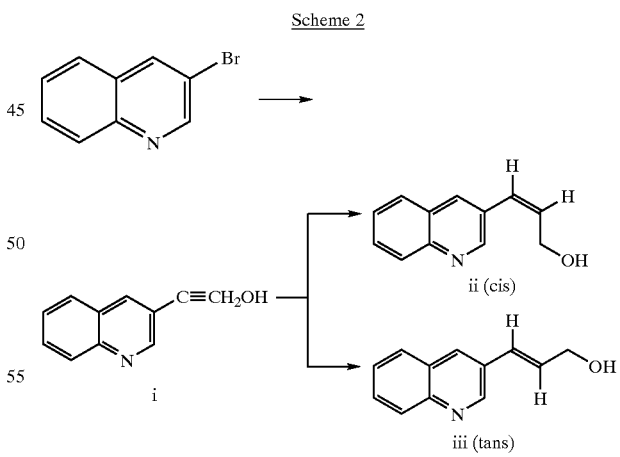

According to Scheme 2, commercially available 3-bromoquinoline is reacted with propargyl alcohol in the presence of an organic base, palladium catalyst and a copper halide or a phase transfer agent, such as tetrabutylammonium bromide. The reaction is carried out at a temperature from about 40° C. to about 90° C.

The 3-(3-quinolyl)-2-propyn-1-ol (i) thus obtained is then reduced by one of the two methods to produce 3-(3- quinolyl)-2-propen-1-ol. The reduction may be accomplished either by catalytic hydrogenation using hydrogen gas and a palladium or a platinum catalyst at room temperature to produce the cis-isomer or using a metal hydride type reagent, for example aluminum hydride reagents. Reaction with lithium aluminum hydride (LAH) and sodium bis(2-methoxyethoxy)aluminum hydride in toluene (Red-Al) between −20° C. to about 25° C. produce the trans-isomer. Certain additives are suitable for the catalytic hydrogenation reaction and can afford the cis-isomer in good yield. One suitable additive is 3,6-dithia-1,8-octanediol, however, various other additives can be used in the hydrogenation.

The 3-(3-quinolyl)-2-propen-1-ol obtained above is then converted into a carbonate by reaction with a wide variety of reagents or into a carbamate by known literature methods, as shown below,

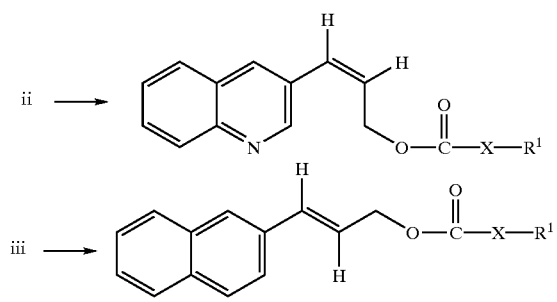

wherein X and $R^1$ are as previously defined. For example, the allylic alcohol, 3-(3-quinolyl)-2-propen-1-ol can be reacted with di-t-butyl dicarbonate at 0° C. in the presence of a hydroxylic base, such as sodium hydroxide to give the corresponding carbonate. See, Houlihan et al., *Can. J. Chem.* 1985, 153.

Compounds of formula (II) are then converted into the compounds of formula (III) by optional deprotection and deoximation. The deprotection of the oxime hydroxyl group is carried out under neutral, acidic or basic conditions depending upon the nature of the protecting group. Conditions for deprotecting a protected oxime of the formula N—O—C(O)—$R^3$ include, but are not limited to, treatment with an alcoholic solvent at room temperature or reflux or treatment with a primary amine, such as butylamine. Alcoholic solvents preferred for the deprotection are methanol and ethanol. The protected oxime of formula N—O—C($R^5$)($R^6$)—O—$R^4$ can be converted with aqueous acid in acetonitrile, for example aqueous acetic acid, hydrochloric acid or sulfuric acid. A more thorough discussion of the procedures, reagents and conditions for removing protecting groups is described in literature, for example, by T. W. Greene and P. G. M. Wuts in *Protective Groups in Organic Synthesis,* 3rd ed., John Wiley & Son, Inc., 1999, which is incorporated herein by reference.

Deoximation of the 9-oxime can be carried out according to the methods described in the literature, for example by Greene (op. cit.) and others. Examples of deoximating agents are inorganic nitrite or sulfur oxide compounds such as sodium nitrite, sodium hydrogen sulfite, sodium pyrosulfate, sodium thiosulfate, sodium sulfate, sodium sulfite, sodium hydrogensulfite, sodium metabisulfite, sodium dithionate, potassium thiosulfate, potassium metabisulfite and the like. Examples of the solvents used are protic solvents such as water, methanol, ethanol, propanol, isopropanol, trimethylsilanol, or a mixture of one or more of the mentioned solvents and the like. Some aprotic solvents can be used in the reaction either alone, or in an aqueous solution, for example tetrahydrofuran.

The deoximation reaction is more conveniently carried out in the presence of an acid such as formic acid, acetic acid, citric acid, oxalic acid, tartaric acid, and trifluoroacetic acid. The amount of acid used is from about 1 to about 10 equivalents of the amount of compound of formula (11) used. In a preferred reaction, the deoximation is carried out using sodium sulfite in the presence of an organic acid, such as tartaric acid. The preferred reaction is carried out in tetrahydrofuran and water to afford a corresponding 9-keto erythromycin derivative.

Compound (III) is then reacted with carbonyldiimidazole in the presence of a strong base to convert the 11,12-diol intermediate directly into a 12-acylimidazolide intermediate. Examples of a suitable base include an alkali metal hydride, an amine base, or an amine base catalyst. The preferred bases are sodium hexamethyldisilazide and 1,8-diaza-bicyclo[5.4.0]-undec-7-ene (DBU). Treatment with sodium hexamethyldisilazide and DBU can be followed by treatment with ammonia or ammonium hydroxide to afford the cyclic carbamate. The alkali metal can be sodium, potassium, or lithium and the aprotic solvent can be one of those defined above.

The conversion reaction can be carried out in two steps. The first step involves the reaction of compound (III) with base in the presence of carbonyldiimidazole in an aprotic solvent for about 8 to about 24 hours at temperatures of about −30° C. to about 45° C. to provide the compound of formula (III')

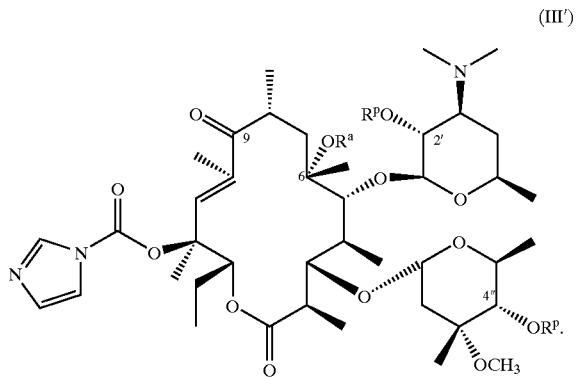

(III')

The reaction can require cooling or heating from about −20° C. to about 45° C., depending on the conditions used, and preferably from about 0° C. to about 35° C. The reaction requires from about 0.5 hours to about 10 days, and preferably from about 10 hours to about 2 days, to complete. Portions of this reaction sequence follow the procedure described by Baker et al., *J. Org. Chem.,* 1988, 53, 2340. Compound (III') is then converted into an 11,12-cyclic carbamate by reacting it with ammonia or ammonium hydroxide. A base, such as potassium t-butoxide, can be optionally added to faciliate the cyclization.

Alternatively, the 11,12-diol is treated with a methanesulfonyl derivative followed by treatment with an amine base to give a 1,2-dihydroxy enone intermediate of the formula:

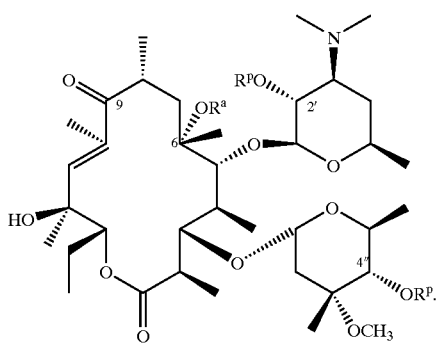

(III″)

The preferred reagent for preparing compound (III″) is methanesulfonic anhydride in pyridine, followed by an amine base, such as DBU in acetone or benzene. Treatment of compound having the formula (III′) with 1,1′-carbonyldiimidazole gives a compound of formula (III′). Treatment of compound of formula (III′) with ammonia optionally in the presence of base converts the 12-acylimidazolide intermediate into an 11,12-cyclic carbamate.

The cladinose moiety of the macrolide can be removed by hydrolysis in the presence of a mild aqueous acid to provide 2. Representative acids include dilute hydrochloric acid, sulfuric acid, perchloric acid, chloroacetic acid, dichloroacetic acid or trifluoroacetic acid. Suitable solvents for the reaction include methanol, ethanol, isopropanol, butanol and the like. Reaction times are typically 0.5 to 24 hours. The reaction temperature is preferably from about −10° C. to about 60° C.

The 3-hydroxyl group of 2 can be oxidized to the ketone (IV) using a modified Swern oxidation procedure or Corey-Kim oxidation conditions. In one method, a diacyl chloride, such as oxalyl chloride, promotes the activation of a suitable oxidizing agent, for example, dimethyl sulfoxide, to give the dimethyl alkoxysulfonium salt of 2. Treatment of the resulting intermediate with a secondary or tertiary amine base affords the corresponding ketone. The preferred bases for the reaction are diethylamine, triethylamine and Hunig's base.

Other suitable oxidizing agents include, but are not limited to, N-chloro-succinimide-dimethyl sulfide, carbodiimide-dimethylsulfoxide, and the like. In a typical example, compound 2 is added into a pre-formed N-chlorosuccinimide and dimethyl sulfide complex in a chlorinated solvent such as methylene chloride at −10 to 25° C. After being stirred for 0.5–4 hours, a tertiary amine, such as triethylamine or Hunig's base, is added to produce the corresponding ketone.

Alternatively, a compound containing a ruthenium transition metal is suitable for carrying out the oxidation reaction in an organic solvent. An exemplary reagent is tetrapropyl-perruthenate (TPAP). The preferred solvent for the reaction is methylene chloride.

Deprotection of the 2′-hydroxyl group provides the desired ketolide (IV). When the protecting group is an ester such as acetate or benzoate, the compound may be deprotected by treatment with methanol or ethanol. When $R^p$ is a trialkylsilyl group, the compound may be deprotected by treatment with a source of fluoride in THF or acetonitrile.

According to the alternate procedure shown in Scheme 3, the compound (I′), which is the 9-oxime compound of erythromycin A, is subjected to acid hydrolysis with dilute mineral or organic acid as described previously to remove the cladinose moiety and give compound 3. The 3- and 2′-hydroxyl groups and the oxime can be appropriately protected with a suitable protecting reagent as previously described, to give the compound 4. The protection is accomplished either simultaneously for the oxime and the hydroxyl groups or in steps, by protecting and isolating each functional group individually with the previously described protecting reagents. Compound 4 is then allylated, deprotected and deoximated as described previously for Scheme 1 to give compound 5. The 2′-hydroxyl and 3-hydroxyl group of compound 5 are optionally protected and reacted with N,N-carbonyldiimidazole and sodium hexamethyldisilazide followed by reaction with ammonia and subsequent deprotection of 2′- and 3-hydroxyl groups to give the carbamate 2. Oxidation of compound 2 affords the compound of formula (IV).

Scheme 3

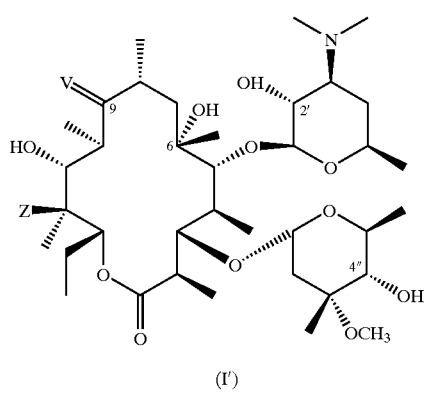

(I′)

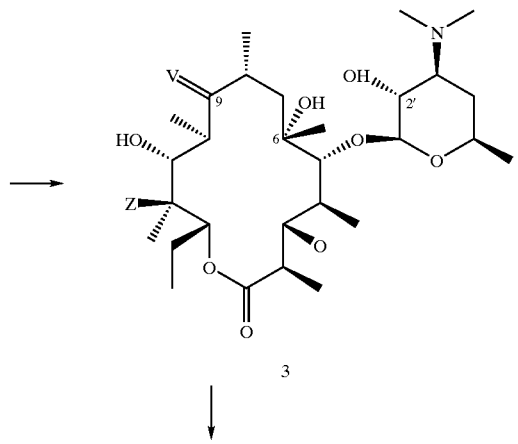

3

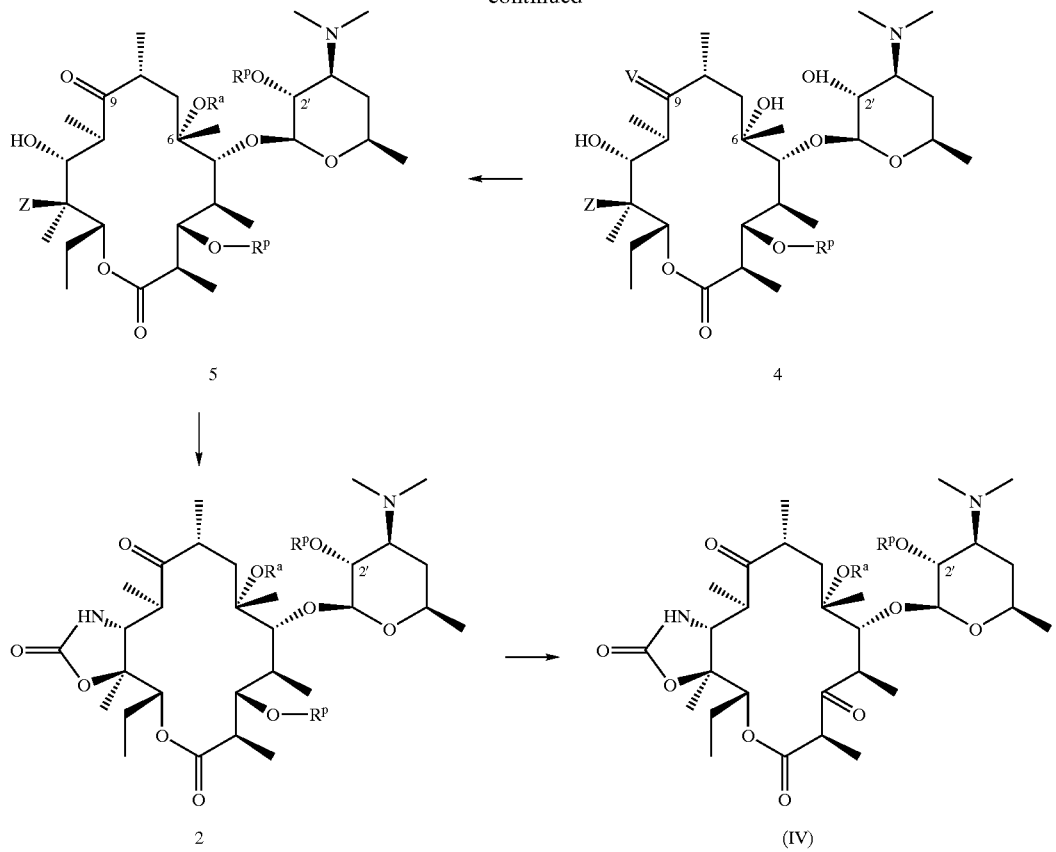

The present invention also relates to intermediate compounds represented by a compound of the formula:

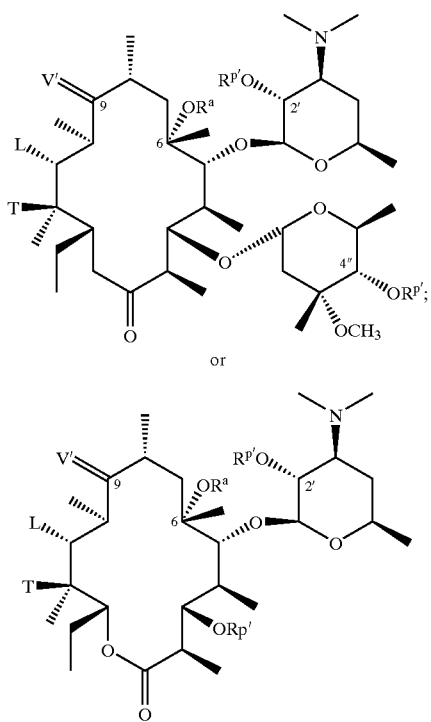

wherein V' is oxygen or N—O—$R^{14}$; wherein $R^{14}$ is selected from the group consisting of acetyl, benzoyl or trimethylsilyl; $R^{p'}$ is independently selected at each occurrence from acetyl, benzoyl or trimethylsilyl; L and T are each hydroxyl; or L taken together with T forms an 11,12-carbamate; and $R^a$ as previously defined. Preferably, $R^{14}$ and $R^{p'}$ are each acetyl or benzoyl.

In a preferred embodiment, $R^a$ is 3-(3-quinolyl)-2-propenyl or 2-allyl, and $R^{p'}$ is benzoyl.

Abbreviations

Abbreviations used in the examples are: Ac for acetyl; THF for tetrahydrofuran; CD1 for 1,1'-carbonyldimethylformamide; DBU for 1,8-diazabicyclo[5.4.0]-undec-7-ene; DMSO for dimethylsulfoxide; and TMSCl for trimethylsilyl chloride; dppb for 1,4-bis(diphenylphosphine)butane; $Pd_2(dba)_3$ for tris(dibenzylideneacetone)dipalladium; IPAC for isopropyl acetate; MTBE for methyl t-butyl ether; DMAP for N,N-dimethylamino-pyridine; and IPA for isopropyl alcohol.

Starting materials, reagents and solvents were purchased from Aldrich Chemical Company (Milwaukee, Wis.), unless otherwise noted below.

The compounds and processes of the invention will be better understood in connection with the Reference Examples and Example s, which are intended as an illustration of and not a limitation upon the scope of the invention as defined in the appended claims.

REFERENCE EXAMPLES

The following Reference Examples illustrate the preparation of suitable alkylating agents for the process of the invention. The alkylating agents provide a group represented by $R^a$, as previously described, which can be attached to the 6-O-position of an erythromycin or ketolide derivative. The Reference Examples, below, are not intended to describe the preparation of an exhaustive list of alkylating agents for the invention.

Reference Example 1

Preparation of allyl t-butyl carbonate

The starting materials and the amounts used are set forth in Table 1 below.

TABLE 1

| Starting Materials | Mol. Weight | Amount Used | Moles | Equiv. |
|---|---|---|---|---|
| Allyl alcohol | 58.08 (d = 0.854) | 149.5 g 175 mL | 2.57 | 1.1 |
| Di-t-butyldicarbonate | 218.25 | 510 g | 2.34 | 1.0 |
| Tetra-n-butylammonium hydrogen sulfate | 339.54 | 39 g | 0.11 | 0.05 |
| Methylene chloride | | 1200 mL | | |
| NaOH (30% w/w in Water) | 40 | 1000 mL | 7.5 | 3.2 |

Methods of preparing the carbonates were carried out in accordance with procedures as described in Houlihan et al., *Can. J. Chem.* 1985, 153. A 3-L three-necked round-bottom flask equipped with mechanical stirring, a nitrogen inlet adapter and a pressure equalizing addition funnel was charged with allyl alcohol, di-t-butyl dicarbonate, and $CH_2Cl_2$ and cooled to 0° C. A 0° C. solution of 30% NaOH (aq.) was added dropwise to the rapidly stirring solution at such a rate that the internal temperature did not rise above 20° C. (about 1 hour). The reaction mixture was stirred at 20° C. for 2 hours prior to work-up.

The crude reaction mixture was partitioned between 1 L water and 500 mL $CH_2Cl_2$. The organic layer was separated, washed with 1 L water and 1 L saturated NaCl solution, dried over $MgSO_4$, filtered and reduced to dryness in vacuo, to afford about 300 g of a yellow oil. The crude product was purified by fractional distillation, bp 96° C. at 70 mmHg, affording the product as a colorless oil, 250.3 g (68%). $^1$H NMR (CDCl$_3$, 300 MHz): δ5.95 (m, 1H), 5.3 (appar quartet of quartets, 2H), 4.55 (appar doublet of triplets, 2H), 1.49 (s, 9H). $^{13}$C NMR (CDCl$_3$, 75 MHz): δ153.1, 131.9, 118.3, 81.9, 67.4, 27.6. MS (NH$_3$, Cl): 176 (M+NH$_4$)$^+$. Anal Calc'd for $C_8H_{14}O_3$: C, 60.73; H, 8.92. Found: C, 60.95; H, 8.96.

Reference Example 2

Preparation of 3-(3-quinolyl)-2-propen-1-ol t-butyl carbonate

Step (1): Preparation of 3-(3-quinolyl)-2-propyn-1-ol (compound (i))

To a dry 2-L three-necked flask previously purged with nitrogen, was charged 3-bromoquinoline (118.77 g, 570 mmol), propargyl alcohol (71.9 g, 1.28 mol, 2.25 equiv), triethylamine (1500 mL), copper(I) iodide (3.62 g, 19 mmol, 0.033 equiv) and dichlorobis(triphenylphosphine) palladium (II) (6.67 g, 9.5 mmol). The resulting mixture was mechanically stirred and heated to reflux for 3 hours. Upon cooling, the triethylamine solution was filtered and washed with triethylamine (300 mL). The filtrate was then concentrated under reduced pressure to provide solids which were suspended in 5% aq. NaHCO$_3$ (600 mL) and extracted with ethyl acetate (1×600 mL). The solids which were left after filtration were treated in the same manner (i.e., suspend in aq. 5% NaHCO$_3$ and extracted with ethyl acetate). The combined ethyl acetate extracts were stirred with silica gel (15 g) and decolorizing carbon (3 g) before being filtered through a bed of diatomaceous earth. The filtrate was concentrated under reduced pressure to provide a tan colored solid which was dried in the vacuum oven at 45° C. overnight. The 3-(3-quinolyl)-2-propyn-1-ol was thus isolated. 92.14 g, 88.3% yield. MS(Cl): (M+H)$^+$ at 184; NMR (300 MHz CDCl$_3$) δ: 4.58 (s, 2H), 4.70 (s, broad, 1H), 7.57 (m,1H), 7.70 (m, 1H), 7.77 (d, 1H), 8.10 (d, 1H), 8.10 (s, H), 9.05 (s, 1H).

Step (2A): Preparation of cis-3-(3-quinolyl)-2-propen-1-ol (compound (ii))

To a 1-L three-necked round-bottom flask was charged 3-(3-quinolyl)-2-propyn-1-ol (31.65 g, 173 mmol), ethanol (550 mL) and 5% palladium on calcium carbonate poisoned with lead (Lindlar catalyst, 750 mg, 0.0024 equiv). The atmosphere above the heterogeneous mixture was purged with hydrogen after which time hydrogen was delivered to the reaction via a balloon. The progress of the reaction was monitored by TLC (1:1 ethyl acetate/heptane). Upon reaction completion (~16 hours), the mixture was purged with nitrogen and vacuum filtered through a bed of diatomaceous earth. The product filtrate was then concentrated under reduced pressure. The residue which resulted was dissolved in ethyl acetate (750 mL) and extracted with 2 N HCl (2×750 mL). The aqueous acidic product solution was then adjusted to pH 9 with 2 N NaOH and then back extracted with isopropyl acetate (2×700 mL). The organic layer was then dried over $Na_2SO_4$, filtered and concentrated to an oil under reduced pressure. The product oil 3-(3-quinolyl)-2-propen-1-ol (29.5 g, 92.2%) consisted of a mixture of both cis and trans alkenols and was subjected to flash chromatography (1:1 ethyl acetate/heptane) to isolate pure cis alkenol.

m.p. 81–82° C. $^1$H NMR (300 MHz, CDCl$_3$) δ8.71 (d, J=2.2 Hz, 1H), 8.04 (dd, J=8.4, 0.9 Hz, 1H), 7.90 (d, J=2.1 Hz, 1H), 7.74 (m, 1H), 7.66 (m, 1H), 7.51 (m, 1H), 66.1 (br d, J=11.8 Hz, 1H), 6.13 (dt, J=11.8, 6.5 Hz, 1H), 4.81 (dd, J=6.4, 1.7 Hz, 2H). $^{13}$C NMR (75 MHz, CDCl$_3$) δ150.8, 146.5, 135.0, 134.4, 129.6, 129.5, 128.7, 127.8, 127.5, 126.9, 126.9, 59.0. Anal. Calc'd for $C_{12}H_{11}NO$: C, 77.81; H, 5.99; N, 7.56. Found: C, 77.89; H, 6.03; N, 7.49.

Step (2B): Preparation of 3-(3-quinolyl) trans-2-propen-1-ol

To a dry 250-mL three-necked jacketed round-bottom flask was charged sodium bis(2-methoxyethoxy)aluminum hydride. (Red-Al, 70% wt. solution in toluene, 11.0 g, 38.1 mmol, 1.39 equiv) and anhydrous THF (20 mL). To this precooled (0–2° C.) and magnetically stirred solution was added a THF (50 mL) solution of the 3-(3-quinolyl)-2-propyn-1-ol (5.0 g, 27.32 mmol) via a pressure equalizing dropping funnel. The temperature was not allowed to rise above 15° C. After the addition was complete (20 minutes) the mixture was allowed to warm up to room temperature and stirred for one hour. The solution was then cooled back to 0° C. and quenched by the addition of aqueous 10% sulfuric acid (20 mL) such that the internal temperature did not rise above 15° C. The biphasic reaction mixture was then basified to pH 9–10 with aq. conc. NH$_4$OH and the aqueous layer was back extracted with ethyl acetate (2×125 mL). The combined organic layers were dried over anhydrous sodium sulfate, filtered and concentrated under reduced pressure to give exclusively 3-(3-quinolyl) trans-2-propen-1-ol as a solid: 4.1 g, 81%.

$^1$H NMR (300 MHz, DMSO-δ6): 9.17 (d, J=2.5 Hz, 1H), 8.39 (d, J=2.5 Hz, 1H), 8.10–8.0 (m, 2H), 7.82–7.64 (m, 2H), 6.90–6.75 (m, 2H), 5.15 (t, J=5.6 Hz, 1H), 4.30 (dd, J=5.6, 3.0 Hz, 2H), 3.51 (s, 1H). $^{13}$C NMR (75 MHz,

DMSO-d6): d 149.3, 146.7, 133.6, 131.8, 130.0, 129.0, 128.7, 128.0, 127.4, 126.9, 125.0, 61.5. Anal. Calc'd for $C_{12}H_{11}NO$: C, 77.81; H, 5.99; N, 7.56. Found: C, 77.75; H, 5.83; N, 7.50.

Step (3): Preparation of 3-(3-quinolyl)-2-propen-1-ol t-butyl carbonate

To a 500-mL three-necked round-bottom flask equipped with an overhead mechanical stirrer was charged 3-(3-quinolyl)-2-propen-1-ol (13.03 g, 70.43 mmol) as a mixture of cis and trans isomers (81% cis, and 19% trans), di-t-butyl dicarbonate (16.91 g, 77.48 mmol, 1.11 equiv), tetra n-butyl ammonium hydrogensulfate (742 mg, 2.17 mmol) and methylene chloride (135 mL). The stirred mixture was cooled to 0 to 5° C. at which time aqueous 25% sodium hydroxide (33.3 mL) was added over 45 minutes such that the internal temperature did not rise above 20° C. Upon completion of the reaction (1 to 4 hours), the reaction mixture was diluted with methylene chloride (50 mL) and washed with water (2×125 mL). The organic layer was dried over anhydrous sodium sulfate, filtered, and concentrated in vacuo to provide the 3-(3-quinolyl)-2-propen-1-ol t-butyl carbonate: 18.35 g (91.4%) as an oil. This material can be further purified by chromatography on silica gel to provide purified carbonate as a colorless oil which retains the original ratio of cis and trans isomers: 17.50 g, 87.2%.

For cis isomer: m.p. 57–58° C. $^1$H NMR (300 MHz, CDCl$_3$) δ8.78 (d, J=2.2 Hz, 1H), 8.07 (m, apparent d, J=8.5 Hz, 1H), 7.93 (d, J=2.0 Hz, 11H), 7.78 (dd, J=8.1, 1.0 Hz, 1H), 7.68 (m, 1H), 7.52 (m, 1H), 6.76 (br d, J=11.7 Hz, 1H), 6.05 (dt, J=11.8, 6.6 Hz, 1H), 4.88 (dd, J=6.6, 1.7 Hz, 2H), 1.47 (s, 9H). $^{13}$C NMR (75 MHz, CDCl$_3$) δ153.1, 150.8, 147.0, 134.7, 129.5, 129.3, 129.1, 128.8, 127.8, 127.4, 126.9, 82.4, 63.3, 27.6. Anal. Calc'd for $C_{17}H_{19}NO_3$: C, 71.56; H, 6.71; N, 4.91. Found: C, 71.31; H, 6.62; N, 4.91.

For trans isomer: m.p. 55–56° C. $^1$H NMR (300 MHz, CDCl$_3$): δ9.00 (d, 1H), 8.08 (br dd, 1H), 7.80 (dd, 1H), 7.72–7.65 (m, 1H), 7.58–7.51 (m, 1H), 6.83 (br d, J=16.2 Hz, 1H), 6.52 (dt, J=16.2, 5.9 Hz, 1H), 4.80 (dd, J=5.9, 1.1 Hz, 1H), 1.52 (s, 9H). $^{13}$C NMR (75 MHz, CDCl$_3$): δ153.2, 149.1, 147.6, 132.9, 130.6, 129.4, 129.2, 129.0, 127.8, 126.9, 125.4, 82.4, 67.0, 27.7. Anal. Calc'd for $C_{17}H_{19}NO_3$: C, 71.56; H, 6.71; N, 4.91. Found: C, 71.59; H, 6.81; N, 4.80.

Reference Example 3

Preparation of Cis-3-(3-quinolyl)-2-propen-1-ol t-butyl carbonate

Step (1): Preparation of Cis-3-(3-quinolyl)-2-propen-1-ol

To a dry 3000-mL three-necked jacketed flask, equipped with a thermocouple was charged 3-(3-quinolyl)-2-propyn-1-ol (76 g, 415.3 mmol), 5% Pd/CaCO$_3$ (1.52 g) and 3,6-dithia-1,8-octanediol (0.76 g). 3A Ethanol (1125 mL) was then charged and the mixture which resulted was vigorously stirred at ambient temperature (19° C.). The atmosphere above the mixture was purged with hydrogen and then evacuated. This purging and evacuating process was repeated twice. Hydrogen balloons (0.32 psi) were placed above the reaction mixture and the progress of the reduction was monitored by HPLC analysis. After 25 hours, the reaction was stopped.

The mixture was filtered through a bed of diatomaceous earth and the flask and cake were washed with 3A ethanol. The filtrate was concentrated under reduced pressure. The residue was dissolved in methyl isobutyl ketone (MIBK, 400 mL) and this solution was passed through a plug of filter aid (38 g). MIBK (125 mL) was used to rinse the flask and cake until the filtrate was colorless. The combined filtrates were concentrated to a volume of 200 mL then diluted with MIBK (270 mL) at which time the crystallization of the cis-3-(3-quinolyl)-2-propen-1-ol initiated. The crystallizing solution was then slowly triturated with heptane (270 mL) with stirring and later cooled at 0° C. overnight. The product was washed with cold MIBK/heptane (3:4, 150 mL). The wet cake was dried in a vacuum oven at 50° C. for 6 hours to give cis-3-(3-quinolyl)-2-propen-1-ol (50.0 g, 70.0% yield, adjusted for potency of starting material). Purity as determined by HPLC was 98.9%.

Step (2): Boc Protection of Cis-3-(3-quinolyl)-2-propen-1-ol

The solid cis-3-(3-quinolyl)-2-propen-1-ol (10.0 g, 54.1 mmol), di-t-butyl dicarbonate (17.6 g, 80.6 mmol, 1.5 equiv), toluene (43 g) and tetra-n-butylammonium hydrogensulfate (0.68 g, 2.0 mmol) were combined and stirred (mechanically) in a three-necked round-bottom flask. To this stirring mixture was slowly added an aqueous sodium hydroxide solution (28 g H$_2$O and 7.0 g, NaOH) over 10 minutes. The temperature of the biphasic mixture warmed from 18° C. to 31° C. over 1.5 hours and was allowed to stir overnight at room temperature. The reaction was then diluted with toluene (33 mL) and water (19 mL). The layers were separated (aq. pH 12) and the organic was washed consecutively with water (1×28 mL) and 5% aq. NaCl (1×28 mL). The organic layer was then washed with an aqueous sodium chloride solution (7 g NaCl, 28 g H$_2$O) before concentration under reduced pressure and a bath temperature of 50° C. The oil which resulted was dissolved in heptane (100 g) and concentrated by rotary evaporation (2×). The resulting residue was dissolved in 55 mL of heptane for crystallization. The product was collected at –5° C., washed with cold heptane (10 mL) and vacuum dried at room temperature to provide a white to off-white colored solid (13.6 g, 88.3%). Purity as determined by HPLC was 98.7%.

Reference Example 4

Preparation of allyl iso-propyl carbonate

Isopropyl alcohol (2-propanol, 31.0 mL, 24.3 g, 0.4 mol, 1.1 equiv), pyridine (64.0 mL, 62.6 g, 0.79 mol, 2.1 equiv), and 500 mL methyl tertiary butyl ether (MTBE) were charged to a suitable reaction vessel and cooled to 0° C. A solution of allyl chloroformate (40.0 mL, 45.4 g, 0.38 mol, 1.0 equiv) in 100 mL of MTBE was added over the course of 10 minutes. The reaction mixture was allowed to stir at 0° C. for 30 minutes prior to warming to room temperature (~25° C.) and stirring overnight (~16 hours). The crude reaction mixture was then filtered through a 1-inch plug of diatomaceous earth (which was then washed with 200 mL of MTBE) and the combined organic layers were washed twice with 200 mL of 20% conc. HCl solution, three times with 200 mL of distilled water, dried over MgSO$_4$ and reduced to dryness in vacuo affording 37.4 g (69%) of the crude carbonate as a colorless oil. The crude oil from this experiment was combined with that from an earlier experiment and they were purified together as a single lot by vacuum distillation (b.p. 74–76° C. at 48–53 mmHg pressure). All spectral data is consistent with the proposed structure.

$^1$H NMR (300 MHz, CDCl$_3$) δ: 5.95 (m, 1H), 5.30 (m, 2H), 4.89 (appar septet, 1H), 4.61 (m, 2H), 1.3 (d, 6H); $^{13}$C NMR (75 MHz, CDCl$_3$) δ: 154.2, 131.6, 118.1, 71.5, 67.7, 21.4, MS (DCI-NH$_3$): 145 (M+H)$^+$ Reference Example 5

Preparation of 1-(3-quinolyl)-2-propen-1-ol t-butyl carbonate

To a stirred solution of quinoline-3-carboxaldehyde (3 g, 19.1 mmol) in tetrahydrofuran (15 mL) at –10° C., was added vinyl magnesium chloride solution in THF (11.3 mL, 15 wt. %, d=0.975) at −5 to −10° C. At the end of the addition, HPLC showed the reaction was complete. This brown solution was transferred by cannula to a stirred solution of di-t-butyl dicarbonate (4.4 g, 22.9 mmol) in THF (10 mL) at −10 to −15° C. After the transfer, the reaction mixture was warmed to 0–5° C. for 1 hour. The mixture was cooled back down to −10° C., diluted with 60 mL of methyl t-butyl ether and quenched with a solution of citric acid (4.8 g, 22.9 mmol) in water (27 mL) at <5° C. After 5 hours of mixing, the organic layer was separated, washed with 30 mL of 7% sodium bicarbonate, 2×30 mL water, and filtered. The filtrate was concentrated under vacuum to give a light brown oil (5.5 g). Column chromatography (silica gel, 20:80 EtOAc/hexane) of the crude product gave pure carbonate (4.3 g). Yield was 79.0%.

$^1$H NMR (300 MHz, CDCl$_3$) δ: 8.93 (appar d, 1H), 8.15 (m, 2H), 7.84 (appar dd, 1H), 7.76 (appar dt, 1H), 7.58 (appar dt, 1H), 6.35 (m, 1H), 6.15 (m, 1H), 5.4 (m, 2H), 1.48(s,9H). $^{13}$CNMR (75.5 MHz, CDCl$_3$) δ: 149.8, 147.9, 135.3, 134.3, 131.5, 129.8, 129.3, 128.0, 127.6, 127.0, 90.4, 82.9, 77.1, 27.8. MS (DCI, NH$_3$): 286 (M+H$^+$). Anal Calc'd for C$_{17}$H$_{19}$NO$_3$: C, 71.56; H, 6.71; N, 4.91. Found C, 71.32; H, 6.75; N, 4.82.

Reference Example 6

Preparation of allyl N,N-diisopropyl carbamate

Di-isopropyl amine (39.6 mL, 3 equiv) and 200 mL methyl tertiary butyl ether (MTBE) were charged to a suitable reaction vessel and cooled to 0° C. A solution of allyl chloroformate (40.0 mL, 45.4 g, 0.38 mol, 1.0 equiv) in 100 mL of MTBE was added over the course of 60 minutes. The reaction mixture became very thick and an additional 200 mL of MTBE was added. The reaction mixture was warmed to room temperature and mixed for an additional 12 hours at which time it was filtered through a 1-inch plug of diatomaceous earth and washed twice with 100 mL of 0.1 N HCl, once with 100 mL of distilled water, dried over MgSO$_4$, and reduced to afford 14.37 g of a colorless oil (83%) (>97% pure by GC). Material was pure enough to use without further purification, spectral data is consistent with this structure.

$^1$H NMR (400 MHz, d$_5$-pyridine) δ6.02 (m, 1H), 5.30 (dq, 1H), 5.15 (dq, 1H), 4.72 (m, 2H), 3.95 (br s, 2H), 1.18 (d, 12H). $^{13}$C NMR (100 MHz, d$_5$-pyridine) δ: 155.0, 134.3, 116.7, 65.1, 45.8 (br), 20.6 (br) MS (DCI-NH$_3$): 186 (M+H)$^+$.

EXAMPLES

The Examples disclosed herein describe methods for preparing 6-O-substituted erythromycin and ketolide derivatives. The Examples are intended to provide examples of the manner in which the process of the invention can be accomplished, and should not be construed as limiting the scope of the invention in any way.

Example 1

Preparation of 6-O-allyl-2',4"-O-bis-trimethylsilylerythromycin A-9-(O-isopropoxy-cyclohexylketal) oxime using allyl t-butyl carbonate (Compound (III), Scheme 1)
Step (1): Preparation of 2',4"-bis-trimethylsilylerythromycin A-9-(O-isopropoxycyclohexylketal) oxime
The above compound was prepared by the methods described in U.S. Pat. No. 4,990,602.

Step (2): Preparation of 6-O-allyl-2',4"-O-bis-trimethylsilylerythromycin A-9-(O-isopropoxycyclohexylketal) oxime 2',4"-O-Bis(trimethylsilyl)-erythromycin A 9-(O-isopropoxycyclohexylketal) oxime) (30.0 g, 29.0 mmol, 1 equiv), allyl t-butyl carbonate (6.65 g, 1.45 equiv), palladium acetate (33 mg, 0.005 equiv), triphenylphosphine (330 mg, 0.043 equiv) and 150 mL of THF were charged to a suitable reaction vessel. The reaction mixture was evacuated and flushed with nitrogen gas several times before being heated to reflux for 19 hours. After cooling to room temperature (~25° C.), ~3.0 mL of commercial bleach solution (5.25% NaOCl) was added and the reaction mixture stirred rapidly for 30 minutes. The reaction mixture was filtered to remove a lumpy white precipitate and reduced to dryness in vacuo affording a nearly quantitative recovery of material (~31 g).

The crude product (87% pure by HPLC) was purified by crystallization from 300 mL of 10:1 isopropanol/heptane at 80° C. After cooling to room temperature, the solid product was collected by filtration affording, after drying, 23.94 g of a colorless solid (77%) (>99% pure by HPLC).

mp: 221–223° C. IR (KBr): 3528, 3411, 2968, 2938, 1735, 1461, 1455, 1381, 1365, 1248, 1170, 1114, 1095, 1008, 897, and 840 cm$^{-1}$. $^1$HNMR(400 MHz, CDCl$_3$) δ: 5.88 (m, 1H), 5.11 (m, 1H), 5.05–5.08 (m, 2H), 5.03 (m, 1H), 4.84 (d, J=4.7 Hz, 1H), 4.43 (d, J=6.9 Hz, 1H), 4.21–4.26 (m, 2H), 4.02–4.15 (m, 2H), 3.93 (dd, J=2.2, 1.5 Hz, 1H), 3.89 (dd, J=2.2, 1.51 Hz, 1H), 3.71–3.76 (m, 4H), 3.66 (m, 1H), 3.30 (s, 3H), 3.23 (s, 1H), 3.16 (d, J=12.4 Hz, 1H), 3.12–3.18 (m, 1H), 2.88 (m, 1H), 2.70 (appar q, m, 1H), 2.53 (br m, 1H), 2.37 (appar d, 1H), 2.24 (br s, 6H), 1.92–2.03 (m, 3H), 1.44–1.90 (in, 11H), 1.43 (s, 3H), 1.14–1.28 (m, 23H), 1.08 (appar t, 6H), 0.98 (d, J=7.2 Hz, 3H), 0.85 (t, J=7.6 Hz, 3H), 0.15 (s, 9H), 0.10 (s, 9H). $^{13}$C NMR (100 MHz, CDCl$_3$) δ: 175.5, 169.3, 137.0, 114.8, 103.9, 102.4, 96.4, 80.7, 79.7 (6-C), 78.3, 77.8, 76.7, 74.0 (12-C), 73.4, 73.2, 70.0 (11-C), 67.2, 65.3, 65.2, 65.1, 62.8, 49.6, 44.8, 40.9, 39.2, 37.2, 35.7, 34.5, 33.4, 33.2, 29.5, 26.3, 25.5, 25.2, 24.4, 24.3, 22.9, 22.1, 21.8, 21.5, 21.1, 19.3, 19.0, 16.1, 15.8, 14.8, 10.6, 9.6, 0.9, 0.7. MS (DCI, NH$_3$): 1073 (M+H$^+$). Anal Calc'd for C$_{55}$H$_{104}$N$_2$O$_{14}$Si$_2$: C, 61.53; H, 9.79; N, 2.61. Found C, 61.61; H, 9.73; N, 2.52.

Example 2

Preparation of 6-O-allyl 2',4"-bis-O-trimethylsilyl-erythromycin A 9-(O-isopropoxycyclohexylketal) oxime using allyl iso-propyl carbonate The title compound was prepared according to the method described in Example 1, Step (2) in 80% crude yield but substituting 1.8 molar equivalents of the allyl iso-propyl carbonate prepared in Reference Example 4 for allyl t-butyl carbonate.

Example 3

Preparation of 6-O-[3-(3-quinolyl)-2-propen-1-yl]-2',4"-bis-O-trimethylsilyl-erythromycin A 9-(O-isopropoxycyclohexylketal) oxime The title compound was prepared in 92% crude yield according to the method described in Example 1, Step (2), but substituting 1.2 molar equivalents of the 1-(3-quinolyl)-2-propen-1-ol t-butyl carbonate prepared in Reference Example 5 for allyl t-butyl carbonate. A small portion of this material was purified by chromatography 2:1 heptane/acetone in order to provide an analytical sample for characterization.

¹H NMR (400 MHz, CDCl₃): 9.06 (appar d, 1H), 8.30 (appar d, 1H), 8.04 (appar d, 1H), 7.78 (appar dd, 1H), 7.61 (appar ddd, 1H), 7.48 (appar ddd, 1H), 6.62–6.50 (m, 2H), 5.19 (appar dd, 1H), 4.80 (appar d, 1H), 4.56–4.39 (m, 2H), 4.28–4.24 (m, 2H), 4.13–4.01 (m, 2H), 3.83–3.65 (m, 5H), 3.30–3.15 (m, 6H), 2.91–2.82 (m, 1H), 2.75–2.70 (m, 1H), 2.65–2.51 (m, 1H), 2.35–2.20 (m, 7H), 2.10–1.02 (m, 50H), 0.89–0.82 (m, 4H), 0.16 (s, 9H), 0.12 (s, 9H). ¹³C NMR (100 MHz, CDCl₃): 175.8, 169.3, 150.5, 147.4, 132.4, 131.6, 130.8, 129.2, 128.7, 128.4, 128.0, 126.5, 126.3, 103.9, 102.4, 96.5, 80.7, 79.9, 78.5, 77.6, 77.0, 73.9, 73.4, 73.1, 70.0, 67.2, 65.2, 65.1, 64.4, 62.8, 49.5, 44.9, 40.8, 39.6, 37.3, 35.6, 34.3, 33.5, 33.4, 26.3, 25.5, 24.3, 24.2, 22.9, 22.7, 22.0, 21.8, 21.6, 21.2, 19.4, 18.9, 16.1, 15.6, 14.7, 10.9, 9.5, 0.9, 0.7. Anal. Calc'd. for $C_{64}H_{109}N_3O_{14}Si_2 \cdot H_2O$: C, 63.07; H, 9.18; N, 3.45. Found: C, 63.02; H, 9.07; N, 3.33.

Example 4

Preparation of 6-O-allyl 2',4"-bis-O-trimethylsilyl-erythromycin A 9-(O-isopropoxycyclohexylketal) oxime using allyl-N,N-diisopropyl carbamate The title compound was prepared according to the method described in Example 1, Step (2) in 71% crude yield but substituting 2.9 molar equivalents of the N,N-diisopropyl carbamate prepared in Reference Example 6 for allyl t-butyl carbonate.

Example 5

Preparation of 6-O-[3-(3-quinolyl)-2-propen-1-yl-11,12 cyclic carbamate-3-keto erythromycin A (Compound (IV) Scheme 1)

Step (1): Preparation of erythromycin A 9-oxime 2',4",9-tribenzoate

Solid erythromycin A oxime (2.006 kg, 2.677 mol) was charged to a 50-L round-bottom flask (equipped with stir paddle, thermocouple and nitrogen inlet) and dissolved in isopropyl acetate (IPAC, 15.5 kg). The IPAC was concentrated while periodically adding tetrahydrofuran (THF, 45.6 kg), to a final volume of 22 L (K.F.=5.3 mol %). Dimethylaminopyridine (DMAP, 0.3282 kg, 2.67 mol), triethylamine (1.198 kg, 11.84 mol) and benzoic anhydride (2.547 kg, 11.269 mol) were added in one portion to the flask and stirred at 25° C. for 40 hours. The reaction mixture was chilled to 0–5° C. and N,N-dimethylethylenediamine (0.427 kg, 1.5 equiv vs Bz₂O assayed) was added at a rate to maintain an internal temperature of <10° C. (typically ~40 min). After the addition was complete, the mixture was stirred for approximately 1 hour at +5° C. until no benzoic anhydride remained. The reaction mixture was transferred to a 100-L vessel, and diluted with methyl-t-butyl ether (MTBE, 20 L). The organic layer was washed with 5% KH₂PO₄ solution (2×20 kg). The organic layer was washed with 7% NaHCO₃ solution (20 kg), and 27% NaCl solution (10 kg). The organic layer was concentrated in vacuo to remove THF, while periodically charging IPA (16 L), to a final volume of 12 L (NMR showed no THF present). The slurry was warmed to 45° C. with good agitation and stirred for 1.5 hours. The slurry was cooled to –5° C. and stirred for 1.5 hours. The product was filtered and washed with IPA (3×1 L precooled to –10° C.). The tribenzoate was transferred to trays and dried at 50° C. under vacuum with a nitrogen bleed. The yield was 2.323 kg (82%).

IR 1722, 1450, 1379, 1339, 1262 cm⁻¹; ¹H NMR (CDCl₃): δ0.75 (d, 3H, J=7.7), 0.82 (t, 3H, J=7.3), 0.90 (d, 3H, J=5.1), 1.10 (s, 3H), 1.17–1.18 (3H, d, J=6.9), 1.21 (3H, s), 1.31 (3H, d, J=7.0), 1.38 (3H, s), 1.41 (1H, m), 1.55 (2H, m), 1.73 (1H, dd, J=5.2, 15.3), 1.76 (1H, m), 1.87(1H, m), 1.92–1.96 (1H, m), 2.34 (6H, s), 2.76–2.81 (2H, m), 2.97 (1H, bs), 3.22 (1H, bs), 3.46 (1H,d, J=6.7), 3.52 (3H, s), 3.79–3.86 (3H, m), 3.87 (1H, dd, J=1.3, 9.2), 4.39–4.44 (2H, m), 4.91 (1H, d, J=9.8), 4.93 (1H, d, J=7.6), 5.02 (1H, d, J=4.9), 5.10 (1H, dd, J=3.6, 10.4), 5.15 (1H, dd, 2.4, 10.7), 7.45–7.50 (6H, m), 7.56–7.62 (3H, m), 8.00–8.07 (5H, m); ¹³C (CDCl₃) δ179.4, 175.1, 1.66.1, 165.4, 163.8, 133.3, 133.2, 132.7, 130.7, 129.9, 129.6, 129.5, 129.0, 128.5, 128.4, 128.2, 100.2, 95.7, 83.6, 79.2, 78.8, 74.7, 74.3, 73.0, 72.3, 69.8, 67.7, 63.7, 63.5, 49.6, 44.5, 40.9, 39.0, 37.3, 35.3, 34.6, 31.8, 28.6, 26.4, 25.3, 21.3, 21.2, 21.1, 18.5, 18.2, 16.5, 15.7, 14.9, 10.6, 9.3. MS (ESI) m/z 1061 (MH⁺). Anal. Calcd for $C_{58}H_{80}N_2O_{16}$: C, 65.64; H, 7.60; N, 2.64; O, 24.12. Found: C,65.37; H, 7.42; N, 2.52; O, 24.38.; m.p.=149–152° C.

Step (2): Alkylation of erythromycin A oxime tribenzoate with 3-(3-quinolyl)-2-propen-1-ol, t-butyl carbonate and oxime deprotection Solid erythromycin A oxime tribenzoate (1000.1 g, 0.942 mol) was charged to a 10-L rotary evaporator flask and dissolved in THF (4.066 kg). The THF was evaporated in vacuo, leaving a foamy oil. The foam was redissolved in THF (3.427 kg) and evaporated again. The resulting material was dissolved in THF (3.500 kg) and transferred to a 12-L round-bottomed flask, equipped with a reflux condenser, nitrogen inlet tube, heating mantle and mechanical stirring apparatus. The vessel was deoxygenated. Solid 3-(3-quinolyl)-2-propen-1-ol, t-butyl carbonate (308.9 g, 1.08 mol, 1.15 equiv) was added in one portion followed by the addition of Pd₂(dba)₃ (8.61 g, 0.0094 mol, 0.01 equiv) and dppb (8.02 g, 0.018 mol., 0.02 equiv). The reaction mixture was heated to reflux (65° C.) for approximately 30 minutes until starting material was consumed.

The reaction mixture was chilled to 15° C. Isopropyl alcohol (4.0 L) was added, followed immediately by 2 N NaOH (234 mL, 0.234 mol, 0.5 equiv). Additional sodium hydroxide solution may be added as needed to push the hydrolysis to completion. The reaction mixture was poured into MTBE (12 L) and 7% aqueous NaHCO₃ (8 L) and agitated 4 minutes. On layer resolution, a black interface formed. The layers were separated, and this interface was removed with the aqueous layer. The organics were washed with 23% aqueous NaCl (8 L) and the layers were separated, again removing any black interface with the aqueous layer. The solvents were removed on the rotary evaporator, with the heating bath at 45° C. The remaining foam was dissolved in THF (4 L) and concentrated by rotary evaporation. The procedure was repeated, leaving the desired product as a dry foam that weighed 1262.1 grams.

IR (film, cm⁻¹) 1725, 1598, 1487, 1379, 1342, 1264; ¹H NMR (CDCl₃): δ: 0.77 (3H, d, J=7.3), 0.79 (3H, t, J=7.3), 0.99 (3H, d, J=5.8), 1.05 (3H, d, J=7.0), 1.06 (3H, s), 1.14 (3H, d, J=7.0), 1.16 (3H, d, J=7.0), 1.21 (3H, s), 1.24 (3H, d, J=6.1), 1.37–1.43 (3H, m), 1.50–1.54 (1H, m), 1.56 (3H, s), 1.71 (1H, dd, J=5.2, 15.2), 1.74–1.78 (1H, m), 1.89–1.94 (1H, m), 1.99–2.04 (1H, m), 2.35 (6H, s), 2.47 (1H, d, J=15.0), 2.60 (1H, q, J=7.0), 2.81–2.87 (1H, m), 2.96–3.02 (1H, m), 3.55 (3H, s), 3.67 (1H, dd, J=1.2, 9.8), 3.78 (1H, d, J=5.8), 3.84–3.89 (1H, m), 3.92–3.98 (1H, m), 4.02 (1H, dd, J=7.0, 11.3), 4.12 (1H, dd, J=3.8, 11.3), 4.53–4.58 (1H, m), 4.69 (1H, s), 4.93 (1H, d, J=9.8), 5.01 (1H, d, 6.6), 5.12 (1H, dd, J=8.3, 10.7), 5.25 (1H, dd, J=2.1, 10.7), 6.17 (1H, d, J=16.1), 6.36 (1H, ddd, J=4.9, 7.0, 16.1), 7.40 (1H, t, J=8.2), 7.42–7.50 (5H, m), 7.55–7.63 (3H, m), 7.72 (1H, d, J=1.8), 8.01–8.05 (5H, m), 8.80 (1H, d, J=2.0), 10.59 (1H, bs); ¹³C (CDCl₃) δ174.7, 169.0, 166.2, 165.5, 149.4, 146.3, 133.2, 132.6, 132.5, 131.1, 131.0, 130.6, 130.0, 129.7, 128.5, 128.4, 128.3, 128.2, 128.1, 127.8, 126.3, 126.2, 100.0, 96.2, 79.5, 79.4, 78.9, 78.8, 76.8, 74.0, 73.0, 72.7, 70.6, 67.3, 64.7, 63.8, 63.7, 49.5, 44.4, 40.9, 38.2, 36.6, 35.4, 32.8, 31.8, 25.5, 21.4, 21.2, 19.0, 18.5, 16.5, 16.0, 15.2, 10.7, 9.5. MS (ESI) m/z 1124 (MH⁺). Anal. Calcd for $C_{63}H_{85}N_3O_{15}$: C, 67.30; H 7.62; N, 3.74; O, 21.34 Found: C, 67.02; H, 7.61; N, 3.59; O, 20.99.

Step (3): Erythromycin A-6-O-[3-(3-quinolyl)-2-propen-1-yl]-9-keto-2',4"-dibenzoate Solid erythromycin A-6-O-[3-(3-quinolyl)-2-propen-1-yl]-9-oxime dibenzoate (800 g at 78% potency) (from Step (2) above), L-tartaric acid (0.280 kg), NaHSO₃ (0.2118 kg), H₂O (3.38 kg) and THF (1.2 L) were charged to a 2 gallon vessel. The mixture was heated to 90° C. over 30 minutes and held at 85–90° C. for an additional 90 minutes with good agitation. The reaction mixture was transferred to a 30-L vessel with the aid of 1.6 L of THF and 0.5 L of water and diluted further with ethyl acetate (EtOAc, 2 L). With agitation, 25 % K₂CO₃ solution (3.6 L) was added. The mixture was further diluted with MTBE (2 L), stirred briefly and allowed to settle until the phases were clear. The bottom aqueous layer was removed. The organic layer was found to contain 517.8 g (84%) of the product. The product layer was concentrated to a final volume of 3 L while periodically adding sequentially EtOAc (1.2 L) and then absolute ethanol (EtOH, 8 L). The slurry was cooled to 5° C. and filtered once supernatant levels of the ketone were <8 mg/mL. The solid was washed with cold EtOH (–10° C.; 3×200 mL), transferred to drying trays and dried at 40° C. under vacuum with a slight N₂ bleed for 2 days. The resulting crystalline solid weighed 485.4 g.

IR 1722, 1694, 1265, 1126, 1070 cm⁻¹; ¹H NMR (CDCl₃): δ0.79 (3H, d, J=7.6), 0.84 (3H, t, J=7.4), 0.95 (3H, d, J=6.1), 1.03 (3H, d, J=6.8), 1.04 (3H, s), 1.14 (3H, d, J=7.0), 1.22 (3H, d, J=4.3), 1.23 (3H, s), 1.24 (3H, d, J=4.0), 1.37–1.43 (1H, m), 1.49 (3H, s), 1.57 (1H, d, J=14.0), 1.75–1.79 (3H, m), 1.87–1.92 (1H, m), 1.96–2.02 (1H, m), 2.36 (6H, s), 2.50 (1H, d, J=15.0), 2.59–2.64 (1H, m), 2.85–2.91 (1H, m), 2.99 (1H, q, J=6.4), 3.00–3.05 (2H, m), 3.54 (1H, bs), 3.56 (3H, s), 3.67 (1H, s), 3.77 (1H, dd, J=1.9, 9.7), 3.81 (1H, d, J=5.7), 3.92–3.98 (1H, m), 4.02 (1H, dd, J=7.6, 11.0), 4.19 (1H, dd, J=4.0, 10.8), 4.47–4.52 (1H, m), 4.95 (1H, d, J=9.4), 5.02 (1H, d, J=7.6), 5.05 (1H, d, J=4.9), 5.08–5.12 (1H, m), 5.16 (1H, dd, J=2.4, 11.0), 6.52–6.59 (1H, m), 6.63 (1H, d, J=16.2), 7.44–7.52 (5H, m), 7.58–7.63 (3H, m), 7.79 (1H, dd, J=1.0, 8.6), 8.02–8.06 (5H, m), 8.27 (1H, d, J=1.8), 9.13 (1H, d, J=2.1). ¹³C (CDCl₃) δ220.2, 175.1, 166.1, 165.4, 150.2, 147.4, 133.4, 132.8, 132.7, 130.8, 130.2, 129.8, 129.6, 129.11, 28.8, 128.7, 128.4, 128.3, 128.2, 127.9, 126.4, 99.9, 96.2, 80.0, 79.2, 78.8, 78.7, 76.5, 74.2, 73.0, 72.5, 68.7, 67.9, 67.4, 64.9, 63.8, 63.7, 58.3, 49.5, 45.5, 44.4, 40.9, 38.1, 37.7, 37.4, 35.4, 31.8, 25.6, 21.3, 21.2, 21.1, 21.0, 18.6, 18.3, 16.3, 12.2, 10.7, 9.5. MS (ESI) m/z 1109 (MH+). Anal. Calcd for $C_{63}H_{84}N_2O_{15}$: C, 68.21; H, 7.63; N, 2.53; O, 21.63 Found: C, 67.98; H, 7.50; N, 2.39; O, 21.88. m.p.=214–216° C.

Step (4): Preparation of erythromycin A 6-O-[3-(3-quinolyl)-2-propen-1-yl]-11,12 cyclic carbamate 2',4"-dibenzoate Solid erythromycin A 6-O-[3-(3-quinolyl)-2-propen-1-yl]-11,12 diol 2',4"-dibenzoate (892.2 g, 96.6% potency, 0.778 mol) was charged to a 20-L rotary evaporator flask and dissolved in THF (5.5 L). The THF is evaporated in vacuo, to approximately 25% of the original volume. The residue was redissolved in THF (5.0 L) and evaporated again to approximately 25% of its volume. The material was dissolved in THF (3.5 L) and transferred to a 12-L flask equipped with a 1000-mL pressure-equalizing addition funnel, nitrogen inlet tube and mechanical stirring apparatus. DMF (1.25 L) was added and the resulting heterogeneous suspension was stirred. Solid CDI (495.6 g, 3.05 mol) was added in one portion. A solution of sodium hexamethyldisilazide (NaHMDS, 1.0 M in THF, 1071 mL, 1.071 mole, 1.3 equiv) was added over 65 minutes maintaining the internal temperature at less than 33° C. The reaction was stirred at ambient temperature for 18 h, until HPLC analysis showed complete consumption (<1 area %) of intermediate the 11,12 cyclic carbonate.

The stirring 12-acylimidazolide solution was cooled to –15° C. and NH₃(g) was added by bubbling through a sub-surface inlet tube. The reaction was kept below –5° C. for 1.5 h until HPLC shows less than 1 area % of 12-acylimidazolide.

The temperature of the reaction mixture was increased to room temperature. A solution of potassium t-butoxide (1 M in THF, 918 mL, 0.918 mol) was added to the reaction maintaining the reaction mixture below 35° C. Based on complete disappearance of starting acyclic carbamate and C-10 methyl epimer (<1 area%) by HPLC, the reaction was complete in 1.5 h after addition of potassium t-butoxide (KOtBu). The reaction mixture was poured into a 50-L separatory funnel containing isopropyl acetate (iPrOAc, 13.5 L) and 5% aqueous KH₂PO₄ (13.5 L), agitated, and the layers separated. The organic layer was washed with an additional 5% aqueous KH₂PO₄ (13.5 L) and then with 5% aqueous KH₂PO₄ (6.7 L). The aqueous layers were combined and extracted with iPrOAc (6.7 L). The combined organic layers were washed with 7% aqueous NaHCO₃ (13.5 L) followed by 23% aqueous NaCl (10 L). The organic solution was concentrated and the product crystallized. Isopropanol (4 L) was added and the mixture was concentrated to approximately 25% of the original volume. Isopropanol (3.4 L) was added and the suspension was stirred at 45° C. for 30 minutes, then chilled to 4° C. and stirred at this temperature for 2 hours. The solid product was filtered and washed with 1 L of cold (+2° C.) iPrOH. The product was dried in a vacuum oven at +55° C. over 48 h to give 793.2 grams of white powder. The final product possessed 96.5% potency, 765.4 grams, 87% yield from erythromycin A-6-O-[3-(3-quinolyl)-2-propen-1-yl]-11,12-diol 2',4"-dibenzoate.

IR 1771.3, 1722, 1453, 1265, 1169, 1107 cm⁻¹; ¹H NMR (CDCl₃): δ0.72 (3H, t, J=7.5), 0.78 (3H, d, J=7.7), 0.95 (3H, d, J=6.1), 1.08 (3H, d, J=6.7), 1.14 (3H, d, J=7.3), 1.21–1.24 (9H, m), 1.31 (3H, s), 1.36–1.40 (2H, m), 1.47 (3H, s), 1.58 (1H, dd, J=1.5, 15.0), 1.72–1.86 (5H, m), 2.36 (6H, s), 2.51 (1H, d, J=15.0), 2.59–2.63 (1H, m), 2.81 (1H, m), 2.88 (1H, q, J=7.0), 3.01 (1H, m), 3.56 (3H, s), 3.71 (1H, s), 3.75 (1H, d, J=6.1), 3.85 (1H, dd, J=1.5, 8.8), 3.99 (1H, dd, J=7.6, 11.0), 4.14 (1H, dd, J=6.1, 11.0), 4.51 (1H, m), 4.88 (1H, dd, J=3.0, 9.5), 4.99 (1H, d, J=9.7), 5.05 (1H, d, J=4.9), 5.09 (1H, dd, J=7.7, 10.7), 5.54 (1H, s), 6.40 (1H, ddd, J=6.4, 7.6, 16.9), 6.63 (1H, d, J=16.2), 7.45–7.55 (5H, m), 7.58–7.62 (3H, m), 7.81 (1H, d, J=8.2), 8.03–8.07 (5H, m), 8.23 (1H, d, J=1.9), 9.06 (1H, d, J=2.1). ¹³C (CDCl₃) δ217.9, 175.8, 170.6, 166.1, 165.3 157.9, 149.9, 147.6, 133.4, 132.7, 131.2, 130.7, 129.9, 129.8, 129.7, 129.6, 129.1, 128.9, 128.4, 128.3, 128.2, 128.1, 128.0, 126.6, 100.0, 96.0, 83.7, 79.6, 79.4, 78.7, 78.0, 76.1, 73.0, 72.4, 67.5, 64.9, 63.7, 57.7, 49.6, 45.2, 44.6, 40.8, 39.2, 38.1, 37.3, 35.2, 31.9, 22.3, 21.8, 21.4, 21.2, 21.0, 18.5, 18.4, 15.5, 13.7, 13.4, 10.6, 9.4. MS (ESI) m/z 1134 (MH⁺). Anal. Calcd for $(C_{64}H_{83}N_3O_{15})_{1/2}H_2O$: C, 67.16; H, 7.41; N, 3.67; O, 21.69 Found: C, 67.18; H, 7.24; N, 3.45; O, 21.71. m.p.=166.5–168° C.

Step (5): Preparation of erythromycin A 6-O-[3-(3-quinolyl)-2-propen-1-yl]-11,12-cyclic carbamate-3-hydroxy-2'-benzoate Crystalline erythromycin A 6-O-[3-(3-quinolyl)-2-propen-1-yl]-11,12-cyclic carbamate dibenzoate (750.0 g, 96.5% potency, 0.639 mol) was charged to a 12-L three-necked round-bottom flask, equipped with a thermocouple, nitrogen inlet tube and mechanical stirring apparatus. EtOH (3.64 L) and 2 N HCl (3.64 L) were added and the mixture was heated to 45° C. until the starting material was not detected by HPLC. After cooling to room temperature, the reaction mixture was poured into 10 L of MTBE and 10 L of water, agitated, and the layers separated. The aqueous product-containing layer (bottom) was diluted with 6 L of iPrOAc and treated with 30% $K_2CO_3$ solution (4.2 kg) with good mixing. The layers were separated. The organic solution was concentrated to a slurry, 5 L of iPrOAc was added, and further concentrated to a final weight of 766.2 g.

IR 1771.3, 1727, 1456, 1274, 1159, 1119cm$^{-1}$; $^1$H NMR(CDCl$_3$): δ0.75–0.81 (6H, m), 1.08 (9H, m), 1.25 (3H, d, J=6.7), 1.32 (3H, s), 1.36–1.40 (1H, m), 1.39 (3H, s), 1.42–1.46 (2H, m), 1.71–1.77 (2H, m), 1.80–1.86 (1H, m), 1.98–2.01 (1H, m), 2.29 (6H, s), 2.53–2.59 (1H, m), 2.63–2.69 (1H, m), 2.85 (1H, q, J=6.4), 2.91 (1H, dt, J=4.0, 12.0), 3.37–3.41 (1H, m), 3.53–3.57 (2H, m), 3.72 (1H, s), 3.82 (1H, d, J=1.8), 3.95–3.99 (2H, m), 4.88 (1H, d, J=7.6), 5.04 (1H, dd, J=7.6, 10.4), 5.11 (1H, dd, J=2.7, 10.4) 5.47 (1H, s), 6.37 (1H, dt, J=16, 6.1), 6.65 (1H, d, J=16.2), 7.44–7.46 (2H, m), 7.51 (1H, t, J=7.0), 7.57 (1H, t, J=7.0), 7.65 (1H, s), 7.82 (1H, d, J=6.7), 8.07 (1H, d J=6.7), 8.09 (2H, dd, J=1.5, 7.0), 8.22 (1H, d, J=1.8), 9.06 (1H, d, J=2.1). $^{13}$C (CDCl$_3$) δ217.5, 175.3, 170.6, 165.4, 158.1, 149.5, 147.3, 132.8, 132.7, 130.6, 129.8, 129.3, 129.2, 128.9, 128.7, 128.4, 128.2, 128.1, 126.9, 99.3, 83.8, 80.6, 79.0, 77.4, 75.5, 72.1, 68.8, 67.6, 64.0, 63.2, 58.1, 45.5, 43.9, 40.8, 38.4, 37.2, 36.0, 32.1, 22.3, 21.8, 21.4, 21.0, 20.1, 18.3, 15.3, 13.8, 13.3, 10.4, 7.9. MS (ESI) m/z 872 (MH+). Anal. Calcd for $C_{49}H_{65}N_3O_{11}$: Theory: C, 67.49; H, 7.51; N, 4.82; Found: C, 67.11; H, 7.38; N, 4.60. m.p.=224–226° C.

Step(6): Preparation of erythromycin A 6-O-3-(3-quinolyl)-2-propen-1-yl]-11,12 cyclic carbamate-3-keto-2'-benzoate N-chlorosuccinimide (NCS, 117.2 g, 880.4 mmol) was charged to a 5-L three-necked round-bottomed flask, equipped with a thermocouple, nitrogen inlet tube, mechanical stirring apparatus and addition funnel. CH$_2$Cl$_2$ (740 mL) was added and the mixture was cooled to −15° C. (±5° C.). Dimethyl sulfide (63.68 g, 73.6 mL, 1.026 mol) was added while maintaining the internal temperature at −15° C. (±5° C.). The reaction mixture was stirred for an additional 15 minutes after the addition was complete. Solid erythromycin A 6-O-[3-(3-quinolyl)-2-propen-1-yl]-11,12-carbamate-3-hydroxy-2'-benzoate (734.7 g, 614 mmol, 72.8 % potency) was dissolved in 1.91 L CH$_2$Cl$_2$ and added while maintaining the internal temperature at −15° C. (±5° C.). The reaction mixture was stirred for I hour after the addition was complete. Et$_3$N (70.6 g, 698 mmol) was added while maintaining the internal temperature at −15° C. (±5° C.). The resulting mixture was stirred at −10° C. (±5° C.) for 1 hour. The cold reaction mixture was poured into 6.7 L EtOAc and 2.7 L of 0.5 N aqueous NaOH was added. The layers were agitated and separated. The top product-containing layer was washed with 5% aqueous NaCl (3.3 L) followed by 27% aqueous NaCl (3.3 L). The organic solution was concentrated to a slurry, MTBE (3 L) was added in portions and concentrated to approximately 1.5 L. Hexane (1.4 L) was charged and the suspension stirred for 30 minutes at 45° C. The suspension was cooled to room temperature and stirred until the concentration of ketolide in the supernatant was <5 mg/mL by HPLC. The slurry was filtered and washed with 1:1 hexane/MTBE (4×300 mL). The product was dried to constant weight in a vacuum oven at ±35° C. over 48 h to give 537.8 grams of white powder (97% yield).

IR 1771.3, 1743, 1719, 1697, 1456, 1267.7, 1172, 1104 cm$^{-1}$; $^1$HNMR (CDCl$_3$): δ0.76 (3H, t, J=7.4), 1.01 (3H, d, J=7.9), 1.09 (3H, d, J=6.7), 1.12 (3h, d, J=7.0), 1.21 (3H, d, J=6.1), 1.36 (3H, d, J=16.9), 1.39 (3H, s), 1.44 (3H, s), 1.42–1.48 (1H, m), 1.54 (1H, dd, J=2.5, 14.7), 1.63 (1H, dd, J=11.7, 14.7), 1.75–1.82 (1H, m), 1.85 (ddd, J=3.4, 7.6, 14.5), 2.26 (6H, s), 2.59–2.62 (1H, m), 2.85–2.89 (2H, m), 3.04–3.12 (1H, m), 3.59–3.64 (1H, m), 3.80–3.86 (3H, m), 4.29 (1H, d, J=4.3), 4.59 (1H, d, J=7.6), 4.93 (1H, d, J=3.2, 9.4), 5.03 (1H, dd, J=7.6, 10.6), 5.49 (1H, s), 6.16 (1H, dt, J=16, 6.7), 6.56 (1H, d, J=6.56), 7.44 (2H, t, J=7.6), 7.50 (1H, t, J=7.6), 7.56 (1H, t, J=7.6), 7.64 (1H, t, J=7.6), 7.82 (1H, d, J=7.6), 8.02 (2H, dd, J=1.6, 7.6), 8.06 (1H, d, J=8.4), 8.15 (1H, d, J=2.1), 9.02 (1H, d, J=2.1). $^{13}$C (CDCl$_3$) δ217.3, 205.4, 169.6, 165.2, 157.6, 149.6, 147.6, 132.8, 132.5, 130.5, 129.9, 129.7, 129.6, 129.2, 129.0, 128.5, 128.3, 128.0, 126.7, 100.7, 83.4, 78.8, 77.5, 75.6, 72.0, 69.2, 64.2, 63.5, 58.1, 50.8, 45.7, 45.0, 40.7, 38.7, 37.2, 31.5, 22.5, 20.9, 20.1, 18.0, 14.4, 13.8, 13.6, 10.6. MS (ESI) m/z 870 (MH+). Anal. Calcd for $C_{49}H_{63}N_3O_{11}$: Theory: C, 67.64; H, 7.30; N, 4.83; Found: C, 67.37; H. 7.21; N, 4.53; . m.p.=150–152° C.

Step (7): Preparation of 6-O-[3-(3-quinolyl)-2-propen-1-yl]-11,12 cyclic carbamate-3-keto erythromycin A Crystalline erythromycin A 6-O-[3-(3-quinolyl)-2-propen-1-yl]-11,12 cyclic carbamate-3-keto-2'-benzoate (495.0 g, 99.8% potency, 0.568 mol) was charged to a 5-L three-necked round-bottomed flask, equipped with a thermocouple, nitrogen inlet tube, and mechanical stirring apparatus. MeOH (1.51 kg) was added and the mixture heated to reflux until starting material was not detected by HPLC (typically 14 hours). After cooling to room temperature, the reaction mixture was concentrated to approximately 1 L, and diluted with 97:3 EtOAc/heptane (3 L) and 0.5 N HCl (1.35 L), and agitated. The bottom product-containing layer was removed and the top organic layer was washed further with 0.5 N HCl (0.25 L). The two bottom product-containing layers were combined and washed with 97:3 EtOAc/heptane (1 L). The bottom product-containing layer was diluted with EtOAc (2.5 L) and treated with 15% (w/v) $K_2CO_3$ solution (1.4 L) and the layers separated. The top product-containing layer was concentrated to approximately 1.2 L and seeded with 10 mg of crystalline 6-O-[3-(3-quinolyl)-2-propen-1-yl]-11,12 cyclic carbamate-3-keto erythromycin A in 100 mL heptane. The product was stirred for approximately 1 h at ambient temperature to allow a sufficient seed bed to form. The slurry was diluted further with 1.7 L heptane and concentrated to approximately 2 L. The product was filtered and washed with 9:1 heptane/EtOAc (3×300 mL). The product was dried to a constant weight in a vacuum oven at +42° C. over 24 hours to give 402.0 g (92%) of a white crystalline solid.

IR 1769.7, 1746.7, 1714, 1701, 1457, 1108, 1049 cm$^{-1}$; $^1$H NMR (CDCl$_3$): δ0.79 (3H, t, J=7.5), 1.11 (3H, d, J=6.9), 1.13 (3H, d, J=7.5), 1.17(3H, d, J=6.1), 1.39 (3H, d, J=6.9), 1.40 (3H, d, J=8), 1.43 (3H, s), 1.47–1.53 (1H, m), 1.51–1.54 (1H, m), 1.66 (1H, ddd, J=1.8, 2.0, 12.6), 1.69 (1H, dd, J=1.2, 14.5), 1.81 (1H, d, J=11.9), 1.84–1.90 (1H, m), 2.26(6H, s), 2.44–2.52 (1H, m), 2.61–2.67(1H, m), 2.96(1H, q, J=6.5), 3.16–3.22 (2H, m), 3.53–3.57 (1H, m), 3.71 (1H, dd, J=7.2, 11.9), 3.84(1H, dd, J=6.5, 11.9), 3.91

(1H, s), 3.96 (1H, q, J=6.7), 4.36 (1H, d, J=7.3), 4.40 (1H, d, J=4.7), 4.94 (1H, dd, J=3.2, 9.1), 5.48 (1H, s), 6.16–6.21 (1H, m), 6.5 (1H, d, J=16.0), 7.50 (1H, t, J=6.9), 7.63 (1H, t, J=6.9), 7.82 (1H, d, J=8.1), 8.05 (1H, d, J=8.4), 8.17 (1H, d, J=2.1), 9.02 (1H, d, J=2.3). $^{13}$C (CDCl$_3$) δ217.3, 205.3, 169.6, 157.6, 149.7, 147.6, 132.4, 129.9, 129.6, 129.1, 129.0, 128.5, 128.0, 126.7, 102.9, 83.5, 78.7, 77.5, 76.4, 70.2, 69.5, 65.8, 64.2, 58.1, 50.8, 46.2, 45.0, 40.2, 39.0, 37.3, 28.3, 22.6, 21.1, 20.1, 18.0, 14.4, 14.1, 13.6, 10.6. MS (ESI) m/z 766 (MH+). Anal. Calc'd for $C_{42}H_{59}N_3O_{11}$: Theory: C, 65.86; H, 7.76; N, 5.49; Found: C, 65.69; H, 7.60; N, 4.34; m.p. =211–213° C.

Example 6

Preparation of 6-O-[3-(3-quinolyl)-2-propen-1-yl]-11,12 cyclic carbamate-3-keto erythromycin A (Compound (IV), Scheme 1)

Step (1): Preparation of erythromycin A 9-oxime-2',4'',9-triacetate

Solid erythromycin A oxime (100.2 g, 0.1338 mol) was charged to a 2-L round-bottom flask and dissolved in tetrahydrofuran (400 mL). Dimethylaminopyridine (2.07 gm, 0.013 mol) and triethylamine (62 mL, 0.443 mol) were charged. The solution was cooled to 0–5° C. and acetic anhydride (39 mL, 0.413 mol) was charged over a one half hour period. The solution was stirred overnight. The solution was cooled to 10° C. and triethylamine (6 mL) and acetic anhydride (5 mL) were charged. The solution was stirred overnight. The solution was cooled to 10° C. and triethylamine (1.5 mL) and acetic anhydride (1.5 mL) were charged. The solution was stirred overnight. Water (50 mL) was charged and the solution was stirred for 10 minutes. Ethyl acetate (300 mL) and 5% sodium bicarbonate (200 mL) were charged. The layers were separated and the organic layer was washed with 5% sodium bicarbonate (150 mL) and 15% sodium chloride (150 mL). The organic solution was dried over sodium sulfate and concentrated to an oil (140 g). The oil was dissolved in methyl t-butyl ether (MTBE, 350 mL) and heated to approximately 40° C. Heptanes (400 mL) were charged and the solution was allowed to cool to ambient temperature. The slurry was cooled to 5–10° C. for 5 hours. The product was filtered washed, with heptane/MTBE (2:1, 110 mL), and dried at 50° C. for 18 hours. The yield was 108.58 gm (92%). MS(APCI): 875 (M+H$^+$).

Step (2): Alkylation of Erythromycin A oxime triacetate with 3-(3-quinolyl)-2-propen-1-ol, t-butyl carbonate and deprotection Erythromycin A oxime triacetate (40.0 g, 45.7 mmol) and 3-3-(quinolyl)-2-propen-1-ol, t-butyl carbonate (13.67 g, 48.0 mmol) were charged to a 1-L rotary evaporator flask. Toluene (400 mL) was charged to dissolve the solids. The solvent was removed under vacuum. The residue was dissolved in toluene (400 mL) and the solvent removed under vacuum. The residue was dissolved in tetrahydrofuran (310 mL). Approximately 150 mL of solvent was removed at a pressure of 300 mmol and a bath temperature of 45° C. The residual solution was transferred to a three-neck round-bottom flask and purged with nitrogen. Pd$_2$(dba)$_3$ (418 mg, 0.46 mmol, 0.01 equiv) and dppb (389 mg, 0.091 mmol, 0.02 equiv) were charged into solution. The solution was deoxygenated. The reaction mixture was heated to 65° C. for approximately 1 hour.

The solution was transferred to a 1-L three-neck round-bottom flask and isopropanol (160 mL) was charged. The solution was cooled to 1° C. and a solution of 1 N sodium hydroxide (28.8 mL, 28.8 mmol, 0.63 equiv) was charged while maintaining a temperature of less than 3° C. After 1 hour additional 1 N sodium hydroxide was charged (6.6 mL, 6.6 mmol, 0.14 equiv) and the reaction was stirred for approximately one hour. The reaction mixture was poured into a mixture of 5% sodium bicarbonate (250 mL) and MTBE (500 mL). The phases were separated and the organic phase was washed with 15% sodium chloride (200 mL). The solvents were removed on the rotary evaporator. The remaining foam was dissolved in THF (200 mL) and concentrated by rotary evaporation. The procedure was repeated, leaving the desired product as a dry foam that weighed 53.17 g.

Step (3): Erythromycin A 6-O-[3-(3-quinolyl)-2-propen-1-yl]-9-keto-4''-acetate

Solid erythromycin A-6-O-[3-(3-quinolyl)-2-propen-1-yl]-9-oxime-2',4''-diacetate (38.0 g, from Step 2 above), acetic acid (9.5 mL), NaHSO$_3$ (11.5 g), water (174 mL) and THF (48 mL) were charged to a 1-L three-neck round-bottom flask. The mixture was heated to approximately 70° C. for 6 hours.

The reaction mixture was charged to a solution of ethyl acetate (150 mL) and THF (150 mL). To the mixture 25% potassium carbonate (150 mL) was charged. The two phase mixture was stirred at 33–40° C. and the layers were allowed to settle. The layers were separated and the aqueous layer was extracted at 35–48° C. with a mixture of THF (70 mL) and ethyl acetate (70 mL). The combined organic layers were washed at about 40° C. with 15% sodium chloride (2×120 mL). The organic solution was concentrated under vacuum to give a foam (37 g). The foam was dissolved in methanol (100 mL) and concentrated by rotary evaporation. The procedure was repeated. The resulting residue was dissolved in methanol (ca. 60 mL) and stirred at 44° C. overnight. The mixture was cooled to 0° C. for 1 hour. The solids were isolated by filtration, washed with cold methanol (8 mL) and vacuum dried at 30° C. for 18 hours to provide 17.5 grams of the product as a white solid.

The filtrate was concentrated and the residue dissolved in methanol (22 mL) and water (7 mL). The mixture was stirred overnight. The solids were isolated by filtration, washed with cold methanol/water (3:1, 4 mL), and vacuum dried at 30° C. for 18 hours to provide 2.05 grams of the product.

Step (4): Erythromycin A 6-O-[3-(3-quinolyl)-2-1propen-1-yl]-9-keto-2'-benzoate-4''-acetate Erythromycin A 6-O-[3-(3-quinolyl)-2-propen-1-yl]-9-keto-4''-acetate (12.00 g, 12.72 mm), benzoic anhydride (3.74 g, 16.54 mmol), isopropyl acetate (48 mL), THF (24 mL) and triethylamine (2.67 mL, 19.1 mmol) were charged to a round bottom flask and the mixture was heated to about 55° C. for 9 hours. The solution was cooled to 5° C. and N,N-dimethylethylenediamine (0.4 mL, 3.8 mmol) was charged. The mixture was stirred for 1 hour. The solids were removed by filtration and washed with ethyl acetate (100 mL) and water (50 mL). The combined filtrates were transferred to a separatory funnel and the aqueous layer was removed. The organic layer was washed with 5% sodium bicarbonate (50 mL) and 20% sodium chloride (30 mL). Ethyl acetate (30 mL) was charged and the organic solution was concentrated under vacuum. The residue was dissolved in acetonitrile (30 mL) and concentrated by rotary evaporation. The procedure was repeated. Acetonitrile (40 mL) was charged and the mixture was heated to 45° C. for 25 minutes. The mixture was cooled to 5° C. The solids were isolated by filtration, washed with cold acetonitrile (5 mL), and vacuum dried at 45° C. for 60 hours to provide 12.55 grams of the product.

¹H NMR (400 MHz, CDCl₃) δ: 9.13 (d, 1H), 8.27 (d, 1H), 8.06 (d, 1H), 8.02 (d, 2H), 7.80 (d, 1H), 7.64 (dt, 1H), 7.58 (t, 1H), 7.50 (t, 1H), 7.46 (t, 2H), 6.62 (d, 1H), 6.55 (dq, 1H), 5.15 (dd, 1H), 5.10 (dd, 1H), 4.99 (d, 1H), 4.92 (d,1H), 4.70 (d, 1H), 4.38 (m, 1H), 4.19 (1H, dd), 4.02 (dd, 1H), 3.90 (m, 1H), 3.78 (d, 1H), 3.75 (appar d, 1H), 3.65 (appar s, 1H), 3.54 (s(—OH), 1H), 3.48 (s, 3H), 3.04 (s(—OH), 1H), 2.99 (m, 2H), 2.86 (m, 1H), 2.62 (m, 1H), 2.45 (d, 1H), 2.34 (s, 6H), 2.14 (s, 3H), 1.96 (m, 1H), 1.88 (m, 2H), 1.74 (dd, 1H), 1.68 (dd, 1H), 1.57 (d, 1H), 1.50 (s, 3H), 1.45 (m, 1H), 1.40 (m, 1H), 1.25 (d, 3H), 1.19 (d, 3H), 1.18 (s, 3H), 1.15 (d, 3H), 1.03 (d, 3H), 1.02 (s, 3H), 0.83 (t, 3H), 0.76 (d, 3H). ¹³C NMR (100 MHz, CDCl₃) δ: 220.3, 175.1, 170.4, 165.4, 150.3, 147.4, 132.8, 132.7, 130.8, 130.2, 129.6, 129.2, 128.8, 128.3, 128.2, 128.0, 126.5, 99.8, 96.2, 79.6, 79.2, 78.5, 76.5, 74.3, 72.8, 72.6, 68.7, 67.2, 65.0, 63.5, 63.3, 49.4, 45.5, 44.3, 40.9, 38.2, 37.8, 37.4, 35.3, 32.1, 21.6, 21.3, 21.1, 21.0, 20.9, 18.5, 18.3, 16.3, 15.9, 12.3, 10.7, 9.4. MS(APCI): 1047 (M+H⁺).

Step (5): Preparation of erythromycin A 6-O-[3-(3-quinolyl)-2-propen-1-yl]-9-keto-11,12-cyclic carbamate-3-hydroxy-2'-benzoate To a 250-mL round-bottom flask were charged erythromycin A 6-O-[3-(3-quinolyl)-2-propen-1-yl]-9-keto-2'-benzoate-4"-acetate (4.00 g, 3.82 mm), carbonyldiimidazole (CDI, 2.75 g, 17.0 mm), THF (25 mL) and DMF (8 mL). The mixture was stirred at 18° C. for 20 minutes and then cooled to 3° C. A solution of sodium hexamethyldisilazide (NaHMDS, 1.0M in THF, 6.0 mL, 6 mm) was added over a 10 minute period. The solution was allowed to warm to ambient temperature and stirred overnight.

The mixture was cooled to 5° C. and NH₃(g) was added by bubbling through the solution for 35 minutes. After 2.5 hours NH₃(g) was added by bubbling through the solution for 30 minutes. After 1.5 hours NH₃(g) was added by bubbling through the solution for 20 minutes. The mixture was stirred for 1.5 hours at 5° C. Potassium t-butoxide (KOtBu, 1.0 M in THF, 4.6 mL, 4.6 mm) was charged and the solution was allowed to warm to ambient temperature and stirred for 19 hours. The reaction mixture was poured into 5% KH₂PO₄ (60 mL) and extracted with isopropyl acetate (60 mL). The organic layer was washed with 5% KH₂PO₄ (60 mL) and then 5% KH₂PO₄ (30 mL). The combined 5% KH₂PO₄ washes were extracted with isopropyl acetate (40 mL). The combined isopropyl acetate extracts were washed with 5% sodium bicarbonate (50 mL). The organic layer was concentrated under vacuum. Isopropyl acetate (50 mL) was charged and the solution was concentrated under vacuum to yield 4.38 grams of a white foam.

The above foam (4.26 g), ethanol (30 mL) and 2 N hydrochloric acid (15 mL) were charged to a 100-mL round-bottom flask. The solution was heated to 50–55° C. for 10 hours. The reaction mixture was poured into water (35 mL) and MTBE (40 mL). The layers were separated and the MTBE layer was extracted with 2 N hydrochloric acid (10 mL). The combined aqueous layer were washed with MTBE (40 mL) and then again with MTBE (20 mL). The pH of the aqueous layer was adjusted to pH 9–10 with 25% potassium carbonate (13 mL) and extracted with ethyl acetate (50 mL). The aqueous layer was extracted with ethyl acetate (25 mL). The combined ethyl acetate layers were washed with 15% sodium chloride (20 mL). The ethyl acetate layer was concentrated under vacuum, dissolved in ethyl acetate (35 mL), and concentrated by rotary evaporation. The resulting residue was redissolved in ethyl acetate (35 mL) and concentrated by rotary evaporation. The residue was dissolved in ethyl acetate (10 mL) at 45° C. Heptane (20 mL) was slowly added at 40–45° C. to cause the product to crystallize. The mixture was cooled to ambient temperature and stirred for 1.5 hours. The slurry was cooled to 5° C. for 1 hour. The solids were isolated by filtration, washed with heptane (5 mL) and vacuum dried at 45° C. overnight to provide the product. The yield was 2.62 grams (79%). MS(APCI): 872 (M+H⁺).

Step(6): Preparation of erythromycin A 6-[3-(3-quinolyl)-2-propen-1-yl]-11,12 cyclic carbamate-3-keto-2'-benzoate N-chlorosuccinimide (NCS, 435 g, 3.27 mmol) was charged to a 25-mL three-necked round-bottom flask, CH₂Cl₂ (5 mL) was added and the mixture was cooled to −15° C. (±5° C.). Dimethyl sulfide (0.28 mL, 3.82 mmol) was added while maintaining the internal temperature at −15° C. (±5° C.). The reaction mixture was stirred an additional 30 minutes after the addition was complete. Solid erythromycin A 6-O-[3-(3-quinolyl)-2-propen-1-yl]-11,12-carbamate-3-hydroxy-2'-benzoate (2.00 g, 2.29 mmol) was dissolved in 10 mL CH₂Cl₂ and added while maintaining the internal temperature at −15° C. (±5° C.). The reaction mixture was stirred 1 hour after the addition was complete. Et₃N (0.365 mL, 2.61 mmol) was added while maintaining the internal temperature at −15° C. (±5° C.). The resulting mixture was stirred at −10° C. (±5° C.) for 1.5 hour. The cold reaction mixture was poured into 50 mL EtOAc and 25 mL of 0.5 N aqueous NaOH is added. The layers were agitated and separated. The top product-containing layer was washed with 5% aqueous NaCl (25 mL) followed by saturated aqueous NaCl (25 mL). The organic solution was dried over sodium sulfate and concentrated. The residue was recrystallized from MTBE (6 mL) and heptanes (6 mL). The slurry was filtered at ambient temperature and washed with MTBE/heptane (1:1, 10 mL). The product was dried under vacuum 40° C. overnight to give 1.99 grams of white powder. MS(ESI): 870 (M+H⁺).

Step (7): Preparation of 6-O-[3-(3-quinolyl)-2-propen-1-yl]-11,12 cyclic carbamate-3-keto erythromycin A Crystalline erythromycin A 6-O-[3-(3-quinolyl)-2-propen-1-yl]-11,12 cyclic carbamate-3-keto-2'-benzoate (1.84 g, 2.11 mmol) was charged to a 100-mL round-bottomed flask. MeOH (15 mL) was added and the mixture was heated to reflux until starting material was not detected by HPLC (17 hours). After cooling to room temperature, the reaction mixture was concentrated, and diluted with 97:3 EtOAc/heptane (25 mL) and 0.5 N HCl (15 mL). The bottom product-containing layer was removed and the top organic layer was washed further with 0.a5 N HCl (10 mL). The two bottom product-containing layers were combined and washed with 97:3 EtOAc/heptane (20 mL). The bottom product-containing layer was diluted with 97:3 EtOAc/heptane (40 mL) and treated with 10% (w/v) K₂CO₃ solution to give a pH of 9–10 and the layers separated. The aqueous layer was extracted with 97:3 EtOAc/heptane (40 mL). The combined product containing EtOAc/heptane layer was washed with 15% sodium chloride and dried over sodium sulfate. The organic solution was concentrated to a thick oil. Ethyl acetate (2 mL) and heptanes (4 mL) were charged and the mixture heated to 38° C. to cause the product to crystallize. Heptane (6 mL) was charged and the slurry was heated at 38° C. for 45 minutes. The slurry was cooled to ambient, filtered, washed with 1:9 EtOAC/heptane (10 mL), and vacuum dried at 45° C. for overnight to provide 1.32 g (81%) of a white crystalline solid. MS(ESI): 766 (M+H⁺).

Example 7

Preparation of 6-O-erythromycin A-9-oxime-2',4",9-tribenzoate

Step (1): Preparation of erythromycin A 9-Oxime

A 250-mL round-bottom flask was charged with 80.0 mL MeOH and cooled to 0–5° C. Hydroxylamine (50% aq. solution, 34.8 g, 526 mmol) was added in portions when a gentle exotherm was observed (3 to 10° C.). Methanol solution was stirred for 5 minutes and internal temperature was brought to 1.5° C. Formic acid (10.4 g, 226 mmol) was then added dropwise at a rate such that the temperature of the reaction mixture stayed below 25° C. This cold solution was transferred to a three-necked flask containing erythromycin A (47.6 g, 64.8 mmol). Flask was equipped with a nitrogen-inlet adapter, temperature probe (T-type) and a mechanical stirrer. The temperature of the reaction mixture was raised to 50° C. and stirring continued for 10 h. The reaction mixture was checked by TLC, which revealed that reaction had gone to completion. The reaction mixture was cooled to 23° C. and diluted with 150 mL IPAC followed by addition of 56 g NaOH (6 N). The pH of the reaction mixture was adjusted between pH 11–12, stirred for 5 minutes and contents transferred to a separatory funnel. The aqueous layer was drained and the organic layer was washed with 100 g NaOH (2 N). Karl-Fisher analysis revealed 4.7% (by weight) moisture/water in the organic layer. The product was used directly in Step (2), below.

Step (2): Tribenzoylation of erythromycin A 9-oxime

The organic layer from Step (1), above, was concentrated to obtain a slurry and redissolved in 100 mL IPAC. Solvent was removed under vacuum to azeo-dry the crude oxime. Karl-Fisher analysis of the slurry showed 0.243% water (by weight). This step was repeated one more time with 100 mL IPAC. The slurry was dissolved in 200 mL (1:1) mixture of IPAC/THF. Kf analysis revealed 0.037 wt. % water. DMAP (7.42 g, 60.7 mmol) and $Bz_2O$ (57.7 g, 225 mmol) were charged in a 1000-mL three-neck round-bottom flask equipped with a mechanical stirrer, gas inlet adapter and a temperature probe followed by the IPAC-THF solution of the crude oxime. Agitation was started with addition of oxime solution. $Et_3N$ (26.2 mL, 188 mmol) was added to the reaction mixture and temperature of the reaction mixture was raised to 40° C. The reaction mixture was stirred for 10.5 h at 40° C. and 13–14 h at room temperature. The reaction was monitored by HPLC and at this time HPLC analysis revealed 4% dibenzoate. The reaction mixture was cooled to 0–5° C. and 6.7 mL N,N-dimethylethylenediamine (5.4 g, 1.5 equiv vs $Bz_2O$ assayed) was added. After 20 minutes at 0–5° C., HPLC revealed no benzoic anhydride remaining in the reaction mixture. The reaction mixture was diluted with 50 mL of IPAC and 100 mL of 10% $KH_2PO_4$ was added to the cold reaction mixture. After stirring for 10 minutes, the reaction mixture was transferred to a 1-L separatory funnel and aqueous phase drained. Organic phase was washed with 100 mL $KH_2PO_4$, 7% $NaHCO_3$ (2×100 mL) and 100 mL brine successively. The solvent was removed by rotary evaporation at 50° C. under vacuum to afford a brown gummy solid. An additional 100 mL IPAC was charged into the flask. The crude product was dissolved and the solvent evaporated to dryness by rotary evaporation under vacuum to azeo-dry the product. The crude product was obtained as a brown gummy solid in quantitative yield. The crude material was dissolved in 60 mL of anhydrous acetone at 60° C.; 215 mL of n-heptane was added. White solid started crystallizing out. The reaction mixture was then heated to 62° C. when all the solids dissolved. The reaction mixture was then slowly allowed to equilibrate at room temperature and after stirring at room temperature overnight, the solid product was collected by vacuum filtration. The wet cake was washed with 1:4 acetone/n-heptane (50 mL) cold solution and dried overnight in vacuo at 50° C. to afford the tribenzoate (38.0 g) as a white solid in 56% yield.

The 6-O-erythromycin A-9-oxime-2',4",9-tribenzoate can be used in the process of Example 5, Steps (2)–(7), to provide a compound of formula (IV).

Example 8

Preparation of erythromycin A-9-oxime-2',4",9-tribenzoate

A 2-L three-necked round-bottom flask equipped with a nitrogen-inlet adapter, temperature probe (T-type) and a mechanical stirrer was charged with 500 mL THF at room temperature (22° C.). $PhCO_2Na$ (75.0 g, 521 mmol) was added to THF with stirring followed by PhCOCl (60.4 mL, 521 mmol). The temperature of the reaction mixture went up to 27° C. during this addition. Stirring was continued for 30 minutes and then the erythromycin A 9-oxime (100.0 g, 134 mmol, K.F.=0.63%) was added in 5 portions of approximately 20 g each. The temperature of the reaction mixture was not allowed to exceed 40° C. during the addition of erythromycin A 9-oxime (required periodic cooling with a water-bath). At this stage, the addition funnel was placed between the flask and the nitrogen-inlet adapter, containing $Et_3N$ (57.7 mL, 414 mmol). $Et_3N$ was added dropwise via addition funnel over a period of 15 minutes. The temperature of the reaction mixture was not allowed to exceed 40° C. during the addition of $Et_3N$ (required periodic cooling with a water bath). After complete addition of $Et_3N$, addition funnel was removed, and DMAP (16.31 g, 134 mmol) was added in portions. The reaction mixture, with white solid suspended in it, was stirred for 14 h at 40° C. and at room temperature for 13 h. The reaction mixture was cooled to 0–5° C. (on cooling, the reaction mixture turns into thick slurry like solution) and 5.0 mL N,N-dimethylethylenediamine (1.5 equiv vs $Bz_2O$ assayed) was added. The slurry was diluted with 150 mL THF and continued to stir for additional 1.5 h. The reaction was monitored by HPLC. After 1.5 h at 0–5° C., HPLC revealed negligible amount (0.8%) of benzoic anhydride remaining in the reaction mixture. Reaction mixture was diluted with 200 mL of IPAC and 150 mL of 10% $KH_2PO_4$ was added to the cold reaction mixture. After stirring for 10 minutes, the reaction mixture was transferred to a 2-L separatory funnel and aqueous phase drained. The organic phase was further diluted with 150 mL IPAC and washed with 150 mL 10% $KH_2PO_4$, 7% $NaHCO_3$ (2×150 mL) and 200 mL brine successively. The solvent was removed by rotary evaporation at 50° C. under vacuum. An additional 250 mL of IPAC was charged into the flask, the crude product was dissolved and the solvent evaporated to dryness by rotary evaporation under vacuum to azeo-dry the product. The crude product was obtained as an off-white foam in quantitative yield. It was dissolved in 250 mL anhydrous acetone by heating at 60° C. and 800 mL n-heptane was added. White solid started crystallizing out. After stirring at room temperature overnight, solid product was collected by vacuum filtration. The wet cake was washed with 1:6 acetone/n-heptane (100 mL) at −5° C. and dried overnight in vacuo at 50° C. to afford the erythromycin A 9-oxime-2',4",9-tribenzoate (118.0 g) as a white solid in 82.8% yield.

The erythromycin A 9-oxime-2',4",9-tribenzoate can be used in the process of Example 5, Steps (2)–(7), to provide a compound of formula (IV).

Example 9

Preparation of 6-O-[3-(3-quinolyl)-2-propen-1-yl]-11,12 cyclic carbamate-3-keto erythromycin A-2′,4″-dibenzoate A 500-mL three-necked round bottom flask was fitted with an overhead mechanical stirrer, a temperature probe, and a nitrogen inlet/outlet. To the reaction vessel was charged erythromycin A 6-O-[3-(3-quinolyl)-2-propen-1-yl]-11,12-diol 2′,4″-dibenzoate (Example 5, Step (3)) (50.00 g, 45 mmol), CDI (18.27 g, 113 mmol, 2.5 equiv), followed by DMF (61 mL) and THF (153 mL). The cloudy mixture was stirred at room temperature for about 5 minutes before DBU (10.1 mL, 68 mmol, 1.5 equiv) was added via a syringe. Immediately after DBU was added, the internal temperature increased from 21° C. to 27° C. As the exotherm subsided, all the solids dissolved to give a clear solution. The reaction mixture was then heated overnight at 35° C. HPLC analysis after 15 h showed complete conversion to the 12-acylimidazolide intermediate.

The solution of 12-acylimidazolide intermediate was cooled to <0° C. and ammonia gas was bubbled through (sub-surface) via a needle. The reaction was maintained at −4° C. and monitored by HPLC. Complete consumption of the 12-acylimidazolide intermediate took approximately 5 h.

The reaction mixture was then warmed to 0° C. A solution of potassium t-butoxide (5.56 g, 50 mmol, 1.1 equiv) in THF (50 mL) was added while maintaining the internal temperature below 10° C. After the base was added, the reaction mixture was warmed to room temperature. By HPLC, the reaction was complete within 2 h.

The reaction mixture was cooled to 0° C. and it was slowly quenched with a 4.5 N HCl solution. The pH of the aqueous layer was adjusted to pH 5–6 with the same acid solution (a total of 64 g of 4.5 N HCl was used). The mixture was transferred to a 1-L separatory funnel along with IPAc (113 mL). After mixing and separating the layers, the organic layer was washed with a 5% $NH_4Cl$ solution (150 mL). The resultant organic fraction was concentrated under reduced pressure to give a thick slurry of white solids.

To the crude mixture was added IPA (225 mL). The mixture was reconcentrated to a thick slurry (~75 mL). IPA (190 mL) was added, and the mixture was heated with stirring inside a 45° C. bath for about 1 h. After cooling to room temperature, the mixture was further cooled to 0° C. and stirred at that temperature for 2 h before the solids were filtered. The mother liquor was recirculated to aid the transfer of solids. The solids were then rinsed with cold IPA (56 mL) before drying under reduced pressure at 65° C.

The dry product isolated was 35.42 g white powder, 69.3% yield, 96.0% peak area.

Example 10

Preparation of 2′-O-benzoyl-3-decladinose-3-oxo-6-O-[3-(3-quinolyl)-2-propen-1-yl]-deoxy-11-carboxyamino erythromycin A 11,12-(cyclic carbamate)

(Compound (IV), Scheme 3)
Step (1): Preparation of des-cladinose erythromycin A 9-oxime hydrochloride
(a) Oxime Formation Erythromycin A (75 g, 0.1 mol, 1 equiv) and 150 mL of isopropyl alcohol were charged to a flask. The reaction mixture was stirred to form a slurry. Hydroxylamine (50 mL, 50% aqueous) was charged into the flask and acetic acid (18.7 mL, 0.32 mol, 3.2 equiv) was added to the reaction mixture. The mixture was heated to 50° C. for 30 hours and a precipitate formed. The crude material was used in Step (b) below without further purification.

(b): Hydrolysis of Cladinose

The reaction mixture from Step (1)(a), above, was cooled to about 20° C. Hydrochloric acid (500 mL, 2 N) was added dropwise to the reaction flask and the mixture was warmed to about 35° C. The precipitated solids dissolved in solution to give a clear liquid. Ethyl acetate (300 mL) was charged into the reaction mixture, followed by 600 mL of 20% potassium carbonate to give a solution with a pH of about 10. The aqueous layer was collected and extracted with 200 mL of ethyl acetate. The ethyl acetate layers were combined, washed with 150 mL of water and 100 mL of 15% sodium chloride solution and concentrated in vacuo. Isopropyl acetate (150 mL) was charged into the solution and concentrated again. The residue was dissolved in 500 mL isopropyl acetate and 100 mL of isopropyl alcohol. The solution was stirred and a 15 mL solution of concentrated HCl in 45 mL of isopropyl alcohol was added. A precipitate formed. The reaction mixture was stirred for about 30 min and then cooled 5–10° C., filtered, and washed with isopropyl acetate (2×75 mL). The crude material was dried under nitrogen to yield 71.3 grams of the crude des-cladinose erythromycin A 9-oxime hydrochloride (111% yield).

Step (2): Preparation of 3-des-cladinose erythromycin A 9-(O-isopropoxycyclohexyl ketal) oxime The 3-des-cladinose erythromycin A 9-oxime hydrochloride from Step (1) (150.9 g, 255 mmol, 1 equiv) was mixed in acetonitrile along with isopropyl cyclohexylketal (170.8 mL, 767.4 mmol, 3 equiv). Formic acid (38.2 mL, 895 mmol, 3.5 equiv) was then added. The clear yellow solution was stirred at ambient temperature under $N_2$. After 2–3 hours, the reaction mixture was extracted with hexanes (4×400 mL). The extractions were continued until TLC and HPLC showed that all the ketal agent was removed. The pH of the reaction mixture was adjusted to pH>9 with 2 N NaOH. The aqueous layer was removed and the acetonitrile layer was extracted with half saturated NaCl solution (100–150 mL). The acetonitrile layer was then removed, dried with $Na_2SO_4$ and concentrated to afford a white foam. (176.84 g, 94.7%) Recrystallization in $CH_3CN$ (3–4 mL/g) afforded the product in about 65–75% recovery.

Step (3A): Preparation of 2′-O-benzoyl-3-hydroxyl-3-descladinose-erythromycin A 9-(O-isopropoxycyclohexyl ketal) oxime The compound from Step (2) (20 g, 27.4 mmol, 1 equiv), above, was mixed in isopropyl acetate (100 mL). Benzoic anhydride (1.3 equiv) was added, followed by $Et_3N$ (4.6 mL, 37.85 mmol, 1.2 equiv). The reaction mixture was stirred at ambient temperature under $N_2$ overnight. A half-saturated solution of $NaHCO_3$ solution (50 mL) was added with stirring for about 15–30 minutes. The aqueous phase was removed and the organic phase was washed with a half-saturated NaCl solution. The organic phase was then dried with $Na_2SO_4$ and concentrated to a foam (22.4 g, 98%). The crude product was carried on to the silylation reaction.

Step (3B): Preparation of 2′-O-benzoyl-3-O-trimethylsilyl-3-descladinose-erythromycin A 9-(O-isopropoxycyclohexyl ketal) oxime The compound from Step (3A) above (8.20 g, 9.8 mmol, 1 equiv) was mixed in $CH_2Cl_2$ (80 mL). Trimethylsilyl imidazole (2.9 mL, 19.6 mmol, 2 equiv) was added, followed by trimethylsilyl chloride (1.5 mL, 11.8 mmol, 1.2 equiv). The reaction mixture was stirred at ambient temperature under $N_2$ for 30 min. A half-saturated NaCl solution (25 mL) was then added to the reaction mixture with stirring for 5–10 min. The aqueous layer was removed and the reaction mixture was washed with saturated NaCl. The $CH_2Cl_2$ layer was removed, dried with $Na_2SO_4$ and concentrated to a white foam (9.39 g, 105.4%). The crude product was crystallized in $CH_3CN$ (5 mL/g) to give a white solid (6.96 g, 78.1%).

Step (4): Preparation of 2'-O-benzoyl-3-O-trimethylsilyl-3-descladinose-6-O-[3-(3-quinolyl-2-propenyl)]-erythromycin A ketal oxime To a three-neck round-bottom flask was charged the 2'-O-benzoyl-3-O-trimethylsilyl-3-descladinose erythromycin A ketal oxime from Step (3B) (1.8 g, 2 mmol, 1 equiv) followed by THF (8 mL). The solution was flushed with $N_2$. To the solution was added the 3-(3-quinolyl)-2-propen-1-ol t-butyl carbonate (741 mg, 2.6 mmol, 1.3 equiv) followed by dppb (17 mg, 0.04 mmol, 0.02 equiv) and $Pd_2(dba)_3$ (18 mg, 0.02 mmol). The resulting solution was heated to 66° C. under $N_2$. After refluxing for 1 hour, HPLC indicated that all the starting material was gone. The solvent was removed in vacuo. To the residue was added hexane (50 mL). The resulting mixture was filtered through a bed of diatomaceous earth. The filtrate was extracted with $CH_3CN$ (3×3 mL). The top hexane layer was concentrated in vacuo to give 1.73 g of the desired product as a light yellow solid (80% yield).

Step (5): Preparation of 2'-O-benzoyl-3-decladinose-3-O-hydroxyl-6-O-[(3-quinol-3-yl)prop-2-enyl]erythromycin A A mixture of the 2'-O-benzoyl-3-O-trimethylsilyl-3-descladinose-6-O-[3-(3-quinolyl)-2-propen-1-yl]-erythromycin A ketal oxime (1.07 g, 1.0 mmol), $NaHSO_3$ (572 mg, 5.5 mmol, 5.0 equiv), and L-tartaric acid (750 mg, 5 mmol, 5 equiv) in $H_2O$/THF (5 mL/1.5 mL) was heated to 82° C. for 8 hours. The pH of the resulting mixture was adjusted with 2 N NaOH, the product was extracted with EtOAc (30 mL). The organic layer was washed with brine, dried over $Na_2SO_4$ and concentrated in vacuo to give 794 mg of product as a light yellow solid (94% yield, HPLC purity is 80%).

Step (6): Preparation of 2'-O-benzoyl-3-decladinose-3-O-trimethylsilyl-6-O-[(3-quinol-3-yl)prop-2-enyl] erythromycin A To a 50-mL round-bottom flask was charged 2.01 grams of 2'-O-benzoyl-3-decladinose 3-O-hydroxyl-6-O-[(3-quinol-3-yl)prop-2-enyl]erythromycin A and 10 mL of methylene chloride. The solution was stirred under nitrogen. To the reaction 0.42 mL of trimethylsilyl imidazole was charged followed by 0.12 mL of trimethylsilyl chloride. The mixture was stirred at ambient temperature for 2 hours and 15 minutes. Half-saturated sodium chloride (20 mL) was charged and the mixture stirred for 5 minutes. Methylene chloride (20 mL) was charged and the layers were separated. The methylene chloride layer was washed with 20 mL of half-saturated NaCl. The methylene chloride layer was dried over sodium sulfate and concentrated under vacuum to a foam 2.33 grams (107% yield, HPLC-82.7 peak area %).

Step (7): Preparation of 2'-O-benzoyl-3-decladinose-3-O-trimethylsilyl-6-O-[(3-quinol-3-yl)prop-2-enyl]-11-deoxy-11-carboxyamino erythromycin A 11,12-(cyclic carbamate)

To 2'-O-benzoyl-3-decladinose-3-O-trimethylsilyl-6-O-[(3-quinol-3-yl)prop-2-enyl]erythromycin A (2.3 g, 2.37 mmol, 1 equiv) in a round-bottom flask was charged 10 mL of tetrahydrofuran and the solution was concentrated under vacuum. The residue was dissolved in 8 mL of tetrahydrofuran and 8 mL of dimethylformamide and the solution charged to a 25 mL round-bottom flask containing 1,1'-carbonyldiimidazole (1.54 g, 9.50 mmol, 1 equiv). The solution was cooled to −12° C. Sodium bistrimethylsilylamide in tetrahydrofuran (3.6 mL of a 1 M solution) was charged while maintaining the temperature of the reaction mixture at −12° C. to −8° C. The solution was stirred with cooling for 30 minutes. The solution was warmed to 2° C. and stirred for 1 hour. A precipitate was present. The solution was warmed to 15–20° C. and stirred for 3 hours to give a clear solution. By HPLC the 12-acylimidazolide intermediate was present (88 pa %).

The reaction mixture was concentrated in vacuo to remove tetrahydrofuran. The concentrated reaction mixture was cooled to 10° C. and 8 mL of concentrated ammonium hydroxide was added. A precipitate formed. Isopropanol (4 mL) was added and the reaction mixture was warmed to ambient temperature and stirred at that temperature for 14 hours.

The reaction mixture was poured into 150 mL of ethyl acetate washed with 5% sodium bicarbonate (3×100 mL), washed with 20% sodium chloride (75 mL), dried over sodium sulfate and concentrated under vacuum to yield 2.25 grams of a foam (100% yield, HPLC −87.7 peak area %).

Step (8): Preparation of 2'-O-benzoyl-3-decladinose-3-O-hydroxyl-6-O-(3-quinol-3-yl)prop-2-enyl]-11-deoxy-11-carboxyamino erythromycin A 11,12-(cyclic carbamate)

To a round-bottom flask was charged 75 mg of 2'-O-benzoyl-3-decladinose-3-O-trimethylsilyl-6-O-[(3-quinol-3-yl)prop-2-enyl]-11-deoxy-11-carboxyamino erythromycin A 11,12-(cyclic carbamate) and 1 mL of isopropanol. To the solution was charged 1 mL of 1 N hydrochloric acid and the solution was stirred at ambient temperature for 1 hour and 15 minutes. The reaction mixture was poured into a flask containing 50 mL of ethyl acetate, washed with 5% sodium bicarbonate (2×20 mL) washed with half-saturated sodium chloride (20 mL), dried over sodium sulfate, and concentrated under vacuum to 71 mg of a foam (103% yield, HPLC −78.4 peak area %).

Step (9): Preparation of 3-decladinose-3-oxo-6-O-[(3-quinol-3-yl)prop-2-enyl]-11-deoxy 11-carboxyamino erythromycin A 11,12-(cyclic carbamate) [Compound (IV), Scheme 3]

The title compound was prepared from compound from Step (8) in two steps by methods described in U.S. Pat. No. 5,866,549.

Example 11

Preparation of 6-O-[3-(3-quinolyl)-2-propen-1-yl]-2'-O-benzoyl erythromycin A 9-(O-benzoyl) oxime To a 250-mL three-necked round-bottom flask, equipped with reflux condenser, addition funnel and nitrogen inlet was charged $Pd_2(dba_3)$ (34 mg, 0.037 mmol, 0.03 equiv) and dppb (32 mg, 0.075 mmol, 0.006 equiv). The contents of the flask were purged with nitrogen for 10 minutes. The 2'-O-benzoyl erythromycin A 9-(O-benzoyl)oxime (12.0 g, 12.6 mmol) and 3-(3-quinolyl)-2-propen-1-ol t-butyl carbonate (5.0 g, 17.6 g, 1.4 equiv) were combined and dissolved in THF (75 mL) and added to the flask through the addition funnel in one portion. The resulting yellow solution was heated to reflux for 4 hours, at which time the 2'-O-benzoyl erythromycin A 9-(O-benzoyl)oxime was consumed, as shown by HPLC analysis. The reaction mixture was cooled and filtered through a sintered glass funnel containing 20 g silica gel. The pad was washed with a 50:50 mixture of hexane/acetone and the product was collected and concentrated as a foam, which was crystallized from $CH_3CN$ to afford 8.7 g of product as a light yellow solid (61%) of 98% potency against a known standard.

The above compound can be converted into a compound of formula (IV) by deprotecting the oxime and following the methods described in Example 5, Steps (3)–(7).

Example 12

Preparation of 6-O-allyl erythromycin A oxime 2', 4",9 tribenzoate

In a suitable reaction vessel was placed the erythromycin oxime tribenzoate (5.00 g, 4.71 mmol, 1 equiv) in 50 mL of toluene. The solvent was removed by distillation in vacuo and replaced with 50 mL of anhydrous THF. The THF was similarly removed by distillation and replaced with 50 mL of fresh anhydrous THF. To this solution was added allyl t-butyl carbonate (0.82 g, 5.19 mmol, 1.10 equiv) and the reaction vessel evacuated and purged with nitrogen three times (KF<0.01%). $Pd_2(dba)_3$ (86 mg, 0.02 equiv) and dppb (80 mg, 0.04 equiv) were added and the vessel was evacuated and purged with nitrogen twice more. The reaction mixture was heated to reflux for 3 hrs. After cooling to rt, 1.0 g of filtering aid was added and the suspension stirred for 30 minutes prior to filtering through a ½" plug of diatomaceous earth (with a 50 mL THF rinse). The solution was reduced to dryness affording 5.31 g (~100%) of crude product. The crude solid was dissolved in 100 mL of 70° C. heptane and filtered through a ½" plug of diatomaceous earth and again reduced to dryness. The resultant solid was purified by crystallization from 30 mL of 1:1 $Et_2O$/hexane affording 3.78 g (73%) of product as a colorless solid. A second crop (0.95 g, 18%) was obtained by further cooling the liquors to −10° C. Total isolation 4.73 g (91%). All data was consistent with the desired compound.

mp: 197–198° C., IR (KBr): 3500 (br), 3000, 1730, 1260,1175, 1115, 1055, and 720 $cm^{-1}$. $^1H$ NMR (500 MHz, $CDCl_3$) δ: 8.01–8.08 (m, 6H), 7.53–7.77 (m, 3H), 7.40–7.51 (m, 6H), 5.70–5.80 (m, 2H), 5.21 (m, appar dd, 1H), 5.09 (m, 1H), 5.01–5.06 (m, 2H), 4.93–5.01 (m, 2H), 4.92 (m, appar d, 1H), 4.81 (m, appar dd, 1H), 4.45 (m, 1H), 3.91 (m, 2H), 3.77 (m, 2H), 3.61–3.67 (m, 3H), 3.55 (s, 3H), 3.26 (br s, 1H), 2.98 (m, appar td, 1H), 2.87 (m, 1H), 2.72 (m, appar q, 1H), 2.32 (d, J=8 Hz, 1H), 2.28 (s, 6H), 1.94 (m, 2H), 1.75 (m, 3H), 1.05–1.60 (m, 23H), 0.92 (d, J=6 Hz, 3H), 0.81 (d, J=7.2 Hz, 3H), 0.75 (d, J=7.6 Hz, 3H), $^{13}C$ NMR (125 MHz, $CDCl_3$) δ: 177.6, 174.8, 166.4, 165.8, 163.3, 134.7, 133.5, 133.1, 132.8, 131.0, 130.0, 129.8, 129.7, 129.4, 128.7, 128.5, 128.4, 117.1, 99.8, 96.2, 79.1, 78.8, 78.5, 76.7, 74.1, 73.0, 72.6, 69.5, 67.3, 65.7, 63.7, 63.6, 49.4, 44.2, 40.8, 37.6, 36.5, 35.3, 34.3, 31.6, 28.6, 21.3, 21.21, 21.19, 21.1, 18.9, 18.4, 16.3, 15.9, 15.1, 10.3, 9.3, MS ($APCI^+$, $NH_3$): 1101 ($M+H^+$), 1118 ($M+NH_4+$), Anal Calc'd for $C_{61}H84N_2O_{16}$: C, 66.53; H, 7.69; N, 2.54. Found C, 66.52; H, 7.72; N, 2.52.

The above compound can be converted into a compound of formula (IV) by deprotecting the oxime and following the methods described in Example 5, Steps (3)–(7).

Example 13

Preparation of 6-O-propenylquinoline erythromycin A 9-(O-isopropoxycyclohexylketal)oxime 2',4"bis-trimethylsilyl ether The 2',4"-O-bis(trimethylsilyl)-erythromycin A 9-(O-isopropoxycyclohexylketal) oxime (10.3 g, 10.0 mmol, 1.0 equiv) and trans-3-(3-quinolyl)-2-propen-ol t-butyl carbonate (3.4 g, 12.0 mmol, 1.2 equiv) were dissolved in toluene (100 mL). The toluene was removed by rotary evaporation to azeotropically dry the starting materials. A second portion of toluene (100 mL) was added, and 50 mL was removed by rotary evaporation. The toluene solution was transferred to a flask containing $Pd_2(dba)_3$ (92 mg, 0.1 mmol, 0.01 equiv) and dppb (171 mg, 0.4 mmol, 0.04 equiv). The solution was heated to 70° C. After 3 hours the reaction was complete. After cooling to rt, 1.0 g of filtering aid was added and the suspension stirred for 30 minutes prior to filtering through diatomaceous earth. The solvent was removed by distillation to produce 11.1 g of a yellow solid (92%). A small portion of this material was purified by chromatography (2:1 heptane/acetone) in order to provide an analytical sample for characterization. All data was consistent with the desired compound.

$^1H$ NMR (400 MHz, $CDCl_3$): 9.06 (d, 1H), 8.30 (d, 1H), 8.04 (d, 1H), 7.78 (dd, 1H), 7.61 (ddd, 1H), 7.48 (ddd, 1H), 6.62–6.50 (m, 2H), 5.19 (dd, 1H), 4.80 (d, 1H), 4.56– 4.39 (m, 2H), 4.28–4.24 (m, 2H), 4.13–4.01 (m, 2H), 3.83–3.65 (m, 5H), 3.30–3.15 (m, 6H), 2.91–2.82 (m, 1H), 2.75–2.70 (m, 1H), 2.65–2.51 (m, 1H), 2.35–2.20 (m, 7H), 2.10–1.02 (m, 50H), 0.89–0.82 (m, 4H), 0.16 (s, 9H), 0.12 (s, 9H). $^{13}C$ NMR (100 MHz, $CDCl_3$): 175.8, 169.3, 150.5, 147.4, 132.4, 131.6, 130.8, 129.2, 128.7, 128.4, 128.0, 126.5, 126.3, 103.9, 102.4, 96.5, 80.7, 79.9, 78.5, 77.6, 77.0, 73.9, 73.4, 73.1, 70.0, 67.2, 65.2, 65.1, 64.4, 62.8, 49.5, 44.9, 40.8, 39.6, 37.3, 35.6, 34.3, 33.5, 33.4, 26.3, 25.5, 24.3, 24.2, 22.9, 22.7, 22.0, 21.8, 21.6, 21.2, 19.4, 18.9, 16.1, 15.6, 14.7, 10.9, 9.5, 0.9, 0.7. Anal. Calc'd. for $C_{64}H_{109}N_3O_{14}Si_2 \cdot H_2O$: C, 63.07; H, 9.18; N, 3.45. Found: C, 63.02; H, 9.07; N, 3.33.

The above compound can be converted into a compound of formula (IV) by deprotecting the oxime and following the methods described in Example 5, Steps (3)–(7).

Example 14

Preparation of 2',4"-O-bis(benzoyl)-6-O-(3-(3-quinolyl)-2-propen-1-yl)-erythromycin A 9-[(O-benzoyl)oxime] using trans-3-(3-quinolyl)-2-propen-1-ol t-butyl carbonate To a suitable reaction vessel was charged erythromycin A oxime tribenzoate (41.1 g, 38.6 mmol, 1 equiv) and trans-3-(3-quinolyl)-2-propen-1-ol t-butyl carbonate (12.6 g, 44.2 mmol, 1.15 equiv) in 300 mL of toluene. The solvent was removed in vacuo and 300 mL of THF added (K.F. titration 0.01%). The catalyst, $Pd_2(dba)_3$ (170 mg, 0.005 equiv) and dppb (160 mg, 0.01 equiv), was added and the reaction mixture degassed by evacuation and venting (three times) in a nitrogen environment. The reaction was heated to reflux for 3 hours, cooled to rt and reduced to dryness in vacuo. The crude residue (49 g, 105% theory) was dissolved in 100 mL of $CH_3CN$ at 60° C., filtered and reduced to dryness affording 46.8 g of product (99%) as a pale yellow foam (>96% purity by HPLC).

The above compound can be converted into a compound of formula (IV) by deprotecting the oxime and following the methods described in Example 5, Steps (3)–(7).

Example 15

Preparation of 2',4"-O-bis(benzoyl)-6-O-(3-(3-quinolyl)-2-propen1-yl)-erythromycin A 9-[(O-benzoyl)oxime] using cis-3-(3-quinolyl)-2-propen-1-ol t-butyl carbonate To a suitable reaction vessel was charged erythromycin A oxime tribenzoate (1.06 g, 1 mmol, 1 equiv) and cis-3-(3-quinolyl)-2-propen-1-ol t-butyl carbonate (0.31 g, 1.09 mmol) in 10 mL of THF. The solvent was removed in vacuo and 10 mL of THF added. The catalyst, Pd₂(dba)₃ (9 mg, 0.01 equiv) and dppb (9 mg, 0.02 equiv), was added and the reaction mixture degassed by evacuation and venting to nitrogen three times. The reaction was heated to reflux. After 1 hour, the reaction was 70% complete by HPLC, so an additional 0.08 g of carbonate (0.28 equiv) was added and refluxed overnight. The reaction mixture was cooled to room temperature and 1.0 g of filter aid was added. After mixing 30 minutes, the reaction mixture was filtered through a plug of diatomaceous earth (20 mL THF rinse) and reduced to dryness affording 1.31 g (107% theory). The crude product was purified by column chromatography on silica gel (elution with 1:2 acetone/heptane) yielding 1.10 g (89%) of the desired product as a colorless solid.

The above compound can be converted into a compound of formula (IV) by deprotecting the oxime and following the methods described in Example 5, Steps (3)–(7).

Example 16

Preparation of 2',4"-O-bis(benzoyl)-6-O-[1-(3-quinolyl)-2-propen-1-yl]-erythromycin A 9-[(O-benzoyl)oxime] using 1-(3-quinolyl)-2-propen-1-ol t-butyl carbonate To a suitable reaction vessel was charged erythromycin A oxime tribenzoate (16.20 g, 15.3 mmol, 1 equiv) and 1-(3-quinolyl)-2-propen-1-ol t-butyl carbonate (secondary carbonate) (5.00 g, 17.5 mmol, 1.14 equiv) in 100 mL of toluene. The solvent was removed in vacuo and 50 mL of THF added. The catalyst, Pd(OAc)₂ (34 mg, 0.01 equiv) and dppb (195 mg, 0.03 equiv), was added and the reaction mixture degassed by evacuation and venting to nitrogen three times. The reaction was then heated to reflux. After 4 hour, the reaction was complete by HPLC and the reaction mixture was cooled to rt and filtered through a ¼" plug of silica gel and reduced to dryness to afford 17.73 g of a pale yellow solid (95%, >95% pure by HPLC).

IR (KBr): 2970, 1730, 1265, 1170, and 1060 cm⁻¹. ¹H NMR (400 MHz, CDCl₃) δ: 8.98 (d, J=2 Hz, 1H), 8.18 (J=2 Hz, 1H), 8.02–8.07 (m, 7H), 7.79 (dd, J=1.2, 8.0 Hz, 1H), 7.57–7.65 (m, 4H), 7.41–7.53 (m, 7H), 6.49 (m, 1H), 6.19 (d, J=16 Hz, 1H), 5.30 (dd, J=2.4, 7.0 Hz, 1H), 5.10 (m, 1H), 5.05 (s, 1H), 5.00 (m, 1H), 4.93 (d, J=9.6 Hz, 1H), 4.49 (m, 1H), 4.33 (s, 1H), 4.14 (appar dd, 1H), 3.96 (m, 1H), 3.65–3.91 (m, 5H), 3.56 (s, 3H), 3.25 (s, 1H), 2.93 (m, 1H), 2.91 (m, 1H), 2.74 (appar q, 1H), 2.49 (appar d, 1h), 2.36 (s, 6H), 2.02 (m, 1H), 1.95 (m, 1H), 1.85 (m, 1H), 1.74 (appar dd, 1H), 1.57 (m, 1H), 1.54 (s, 3H), 1.31–1.45 (m, 3H), 1.11–1.28 (m, 12H), 1.14 (d, J=6.8 Hz, 3H), 1.10 (s, 3H), 0.95 (d, J=6 Hz, 3H), 0.87 (t, J=7.2 Hz, 3H), 0.79 (d, J=7.6 Hz, 3H). ¹³C NMR (100 MHz, CDCl₃) δ: 177.4, 175.0, 166.3, 165.7, 163.0, 150.6, 147.6, 133.5, 133.3, 132.8, 130.9, 130.2, 130.0, 129.7, 129.5, 129.4, 129.2, 129.1, 128.9, 128.8, 128.7, 128.5, 128.41, 128.39, 128.2, 127.9, 127.1, 126.4, 125.5, 99.8, 96.3, 79.2, 79.1, 78.71, 78.70, 77.2, 76.9, 74.0, 73.0, 72.6, 69.7, 67.9, 67.3, 64.9, 63.7, 63.6, 49.4, 44.2, 40.8, 37.8, 36.6, 35.2, 34.3, 31.6, 31.1, 29., 28.6, 25.4, 21.3, 21.21, 21.2, 21.0, 18.7, 18.4, 16.3, 15.9, 15.1, 10.5, 9.3. MS (DCI/NH₃): 1228 (M+H⁺). Anal Calc'd for C₇₀H₈₉N₃O₁₆: C, 68.60; H, 7.46; N, 3.34. Found C, 68.43; H, 7.30; N, 3.42.

The above compound can be converted into a compound of formula (IV) by deprotecting the oxime and following the methods described in Example 5, Steps (3)–(7).

What is claimed is:

1. A process for preparing 6-O-substituted erythromycin derivatives comprising reacting an erythromycin derivative with an alkylating agent having the formula:

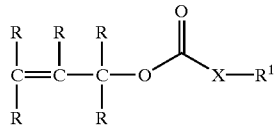

wherein:
R is independently selected from the group consisting of:
hydrogen, an alkyl group of one to ten carbon atoms, halogen, aryl, substituted aryl,
heteroaryl and substituted heteroaryl;
R¹ is an alkyl group of one to ten carbon atoms, and X is O or NR', wherein R' is alkyl or aryl, or R¹ and R' taken together form an aromatic or non-aromatic ring;
in the presence of palladium catalyst and a phosphine.

2. The process according to claim 1, wherein the alkylating agent is selected from the group consisting of allyl iso-propyl carbonate, allyl t-butyl carbonate, allyl N,N-di-isopropyl carbamate, 3-(3-quinolyl)-2-propen-1-ol t-butyl carbonate and 1-(3-quinolyl)-2-propene-1-ol t-butyl carbonate.

3. The process according to claim 2, wherein the alkylating agent is selected from the group consisting of allyl t-butyl carbonate, 3-(3-quinolyl)-2-propen-1-ol t-butyl carbonate and 1-(3-quinolyl)-2-propen-1-ol t-butyl carbonate.

4. The process according to claim 1, wherein the palladium catalyst is selected from the group consisting of palladium acetate, tetrakis(triphenylphosphine)palladium, tris(dibenzylideneacetone)dipalladium, and (tetradibenzylideneacetone)dipalladium.

5. The process according to claim 1, wherein the phosphine is selected from the group consisting of triphenylphosphine, bis(diphenylphosphine)methane, bis(diphenylphosphine)ethane, bis(diphenylphosphine) propane, 1,4-bis(diphenylphosphine)butane, bis(diphenylphosphine)pentane, and tri(o-tolyl)phosphine.

6. The process according to claim 1, wherein the ratio of palladium catalyst to the phosphine ranges from about 2:1 to about 1:8.

7. The process according to claim 1, wherein the erythromycin derivative is represented by the formula:

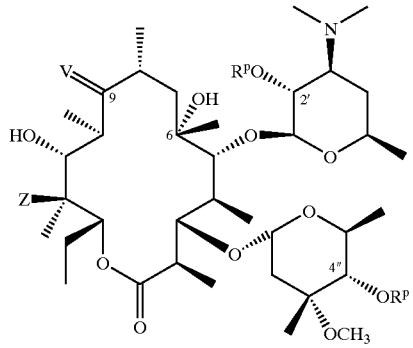

wherein:
R$^P$ is independently hydrogen or hydroxyl-protecting group except that R$^P$ may not be simultaneously hydrogen at both positions;

V is selected from the group consisting of:
a) O
b) an oxime having the formula N—O—$R^2$; wherein
$R^2$ is selected from the group consisting of:
hydrogen,
a loweralkenyl group,
an aryl(loweralkyl) group, and
a substituted aryl(loweralkyl) group;
c) an oxime having the formula

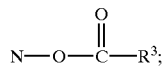

wherein
$R^3$ is selected from the group consisting of:
alkyl,
alkylaryl,
aryl, and
substituted aryl;
d) an oxime having the formula

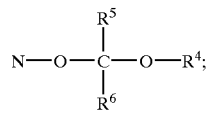

wherein
$R^4$ is selected from the group consisting of:
a loweralkyl group,
a cycloalkyl group,
a phenyl group, and
an aryl(loweralkyl) group;
or $R^4$ and $R^5$ or $R^4$ and $R^6$ and the atoms to which they are attached are taken together to form a 5- to 7-membered ring containing one oxygen atom; and
$R^5$ and $R^6$ are independently selected from the group consisting of:
a hydrogen atom,
a loweralkyl group,
a phenyl group, and
an aryl(loweralkyl) group;
or any pair of substituents selected from ($R^4$ and $R^5$), ($R^4$ and $R^6$) or ($R^5$ and $R^6$) and the atoms to which they are attached are taken together to form a 5- to 7-membered ring optionally containing one oxygen atom; provided that only one pair of substituents ($R^4$ and $R^5$), ($R^4$ and $R^6$) or ($R^5$ and $R^6$) may be taken together with the atoms to which they are attached to form a ring as defined above;
e) an oxime having the formula:

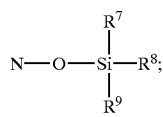

wherein $R^7$, $R^8$, and $R^9$ are independently selected from the group consisting of hydrogen, loweralkyl, aryl-substituted alkyl, aryl, cycloalkyl, and loweralkenyl;

f)

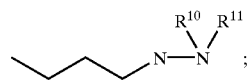

wherein $R^{10}$ and $R^{11}$ are independently selected from the group consisting of hydrogen, alkyl and a nitrogen-protecting group, or $R^{10}$ and $R^{11}$ taken together form a 5- to 7-membered cycloalkyl ring; and g)

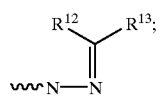

wherein $R^{12}$ and $R^{13}$ are independently selected from the group consisting of hydrogen, alkyl and a nitrogen-protecting group; or $R^{12}$ and $R^{13}$ taken together form a 5- to 7- membered cycloalkyl ring; and
Z is hydroxyl or a protected hydroxyl group.

8. A process for preparing a compound represented by formula:

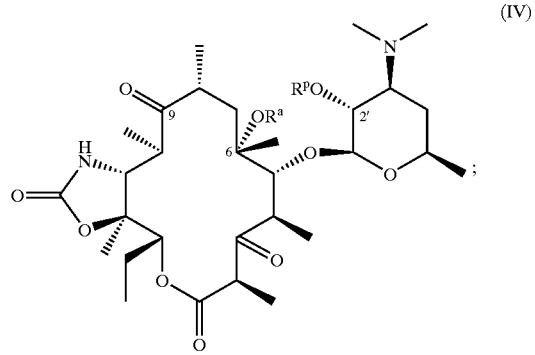

or pharmaceutically acceptable salt, ester or prodrug thereof, wherein
$R^a$ is represented by the formula:

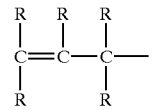

wherein:
R is independently selected from the group consisting of:
hydrogen, an alkyl group of one to ten carbon atoms, halogen, aryl, substituted aryl, heteroaryl and substituted heteroaryl at each occurrence; the process comprising the steps of:
(a) reacting an erythromycin derivative with an alkylating agent having the formula:

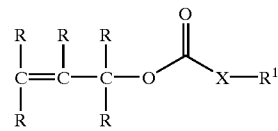

wherein

R is as defined above;

$R^1$ is an alkyl group of one to ten carbon atoms, and

X is O or NR', wherein R' is alkyl or aryl, or $R^1$ and R' taken together form an aromatic or non-aromatic ring;

in the presence of palladium catalyst and a phosphine;

(b) optionally deprotecting and deoximating the 6-O substituted erythromycin of step (a) to obtain the compound of formula:

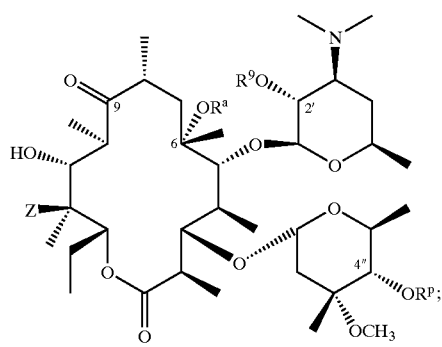
(III)

wherein Z is hydroxyl or protected hydroxyl group and $R^a$ and $R^p$ are as defined above;

(c) reacting the compound from step (b) with 1,1'-carbonyldiimidazole in the presence of an amine base or an amine base catalyst followed by a reaction with ammonia or ammonium hydroxide optionally carried out in the presence of a strong base to afford a compound having the formula:

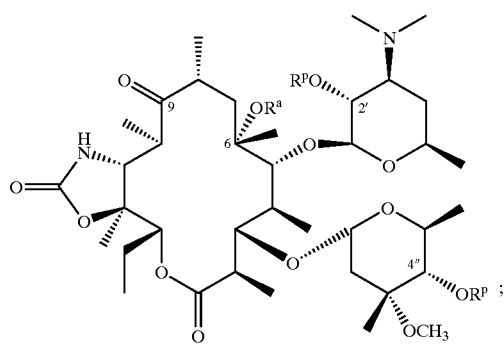

(d) removing the cladinose moiety from the compound obtained in step (c) by hydrolysis with acid to give a compound having the formula

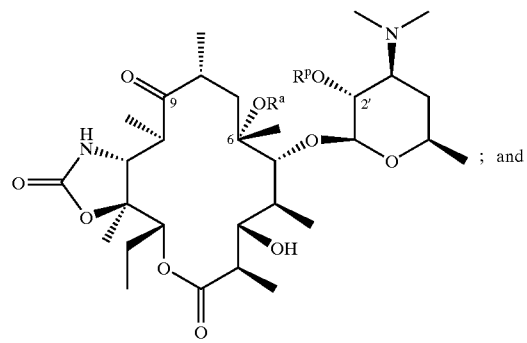
; and (e) oxidizing the 3-hydroxyl group, and optionally deprotecting and isolating the resulting compound.

9. The process according to claim 8, wherein the erythromycin derivative in step (a) is a compound of the formula:

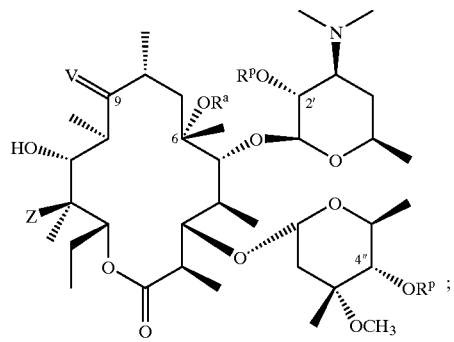
;

wherein $R^p$ is independently hydrogen or hydroxyl-protecting group except that $R^p$ may not be simultaneously hydrogen at both positions;

V is selected from the group consisting of:
 a) O
 b) an oxime having the formula N—O—$R^2$; wherein $R^2$ is selected from the group consisting of:
  hydrogen,
  a loweralkenyl group,
  an aryl(loweralkyl) group, and
  a substituted aryl(loweralkyl) group;
 c) an oxime having the formula

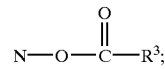

wherein
 $R^3$ is selected from the group consisting of:
  alkyl,
  alkylaryl,
  aryl, and
  substituted aryl;
 d) an oxime having the formula

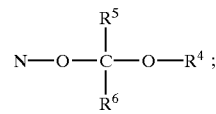

wherein
R⁴ is selected from the group consisting of:
a loweralkyl group,
a cycloalkyl group,
a phenyl group, and
an aryl(loweralkyl) group;
or R⁴ and R⁵ or R⁴ and R⁶ and the atoms to which they are attached are taken together form a 5- to 7-membered ring containing one oxygen atom; and
R⁵ and R⁶ are independently selected from the group consisting of:
a hydrogen atom,
a loweralkyl group,
a phenyl group, and
an aryl(loweralkyl) group;
or any pair of substituents selected from (R⁴ and R⁵), (R⁴ and R⁶) or (R⁵ and R⁶) and the atoms to which they are attached are taken together form a 5- to 7-membered ring optionally containing one oxygen atom; provided that only one pair of substituents (R⁴ and R⁵), (R⁴ and R⁶) or (R⁵ and R⁶) may be taken together with the atoms to which they are attached to form a ring as defined above;
e) an oxime having the formula:

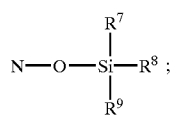

wherein R⁷, R⁸, and R⁹ are independently selected from the group consisting of hydrogen, loweralkyl, aryl-substituted alkyl, aryl, cycloalkyl, and loweralkenyl;
f)

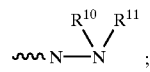

wherein R¹⁰ and R¹¹ are independently selected from the group consisting of hydrogen, alkyl and a nitrogen-protecting group, or R¹⁰ and R¹¹ taken together form a 5- to 7-membered cycloalkyl ring; and
g)

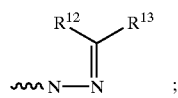

wherein R¹² and R¹³ are independently selected from the group consisting of hydrogen, alkyl and a nitrogen-protecting group; or R¹² and R¹³ taken together form a 5- to 7-membered cycloalkyl ring; and
Z is hydroxyl or a protected hydroxyl group.

10. The process according to claim 9, wherein R$^p$ is acetyl or benzoyl.

11. The process according to claim 8, wherein the erythromycin derivative of step (a) is an erythromycin 9-oxime derivative, said erythromycin 9-oxime derivative is treated with a benzoylating agent.

12. The process according to claim 11, wherein the benzoylating agent is benzoyl chloride or benzoic anhydride.

13. The process according to claim 11, wherein the benzoylating agent is a combination of benzoyl chloride and sodium benzoate.

14. The process according to claim 8, wherein the alkylating agent is selected from the group consisting of allyl iso-propyl carbonate, allyl t-butyl carbonate, allyl N,N-di-isopropyl carbamate, 3-(3-quinolyl)-2-propen-1-ol t-butyl carbonate and 1-(3-quinolyl)-2-propene-1-ol t-butyl carbonate.

15. The process according to claim 8, wherein the palladium catalyst is selected from the group consisting of palladium acetate, tetrakis(triphenylphosphine)palladium, and tris(dibenzylideneacetone)dipalladium, and (tetradibenzylideneacetone)dipalladium.

16. The process according to claim 8, wherein the phosphine is selected from the group consisting of triphenylphosphine, bis(diphenylphosphine)methane, bis(diphenylphosphine)ethane, bis(diphenylphosphine)propane, 1,4-bis(diphenylphosphine)butane, bis(diphenylphosphine)pentane, and tri(o-tolyl)phosphine.

17. The process according to claim 8, wherein the ratio of palladium catalyst to the phosphine ranges from about 2:1 to about 1:8.

18. The process according to claim 8, wherein the 6-O-substituted erythromycin derivative prepared in step (a) is reacted with a sulfur oxide and sodium nitrite.

19. The process according to claim 18, wherein the sulfur oxide compound is sodium hydrogen sulfite, sodium metabisilfite or sodium bisulfite.

20. The process according to claim 19, wherein sodium hydrogen sulfite is reacted with the 6-O-substituted erythromycin derivative in the presence of an organic acid.

21. The process according to claim 20, wherein the reaction is carried out in an aprotic solvent.

22. The process according to claim 20, wherein the acid is tartaric acid.

23. The process according to claim 21, wherein the aprotic solvent is tetrahydrofuran.

24. The process according to claim 8, wherein the amine base or an amine base catalyst in step (c) is sodium hexamethyldisilazide; 1,8-diazabicyclo[5.4.0]-undec-7-ene; or a mixture thereof.

25. A process for preparing a compound of formula:

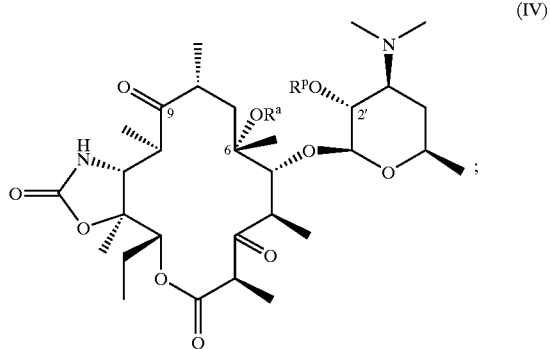

(IV)

or pharmaceutically acceptable salt, ester or prodrug thereof, wherein $R^a$ is represented by the formula:

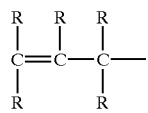

wherein R is independently selected from the group consisting of:
hydrogen, an alkyl group of one to ten carbon atoms, halogen, aryl, substituted aryl, heteroaryl and substituted heteroaryl; the process comprising the steps of:

(a) removing the cladinose moiety from an erythromycin derivative by hydrolysis with an acid to give a compound having the formula

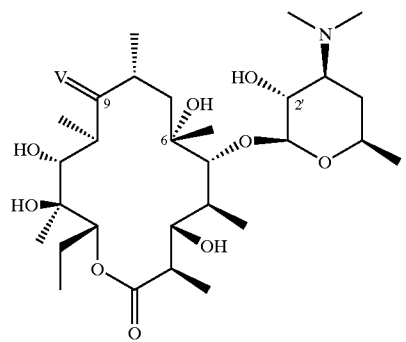

(b) protecting the hydroxyl groups to obtain a compound of the formula

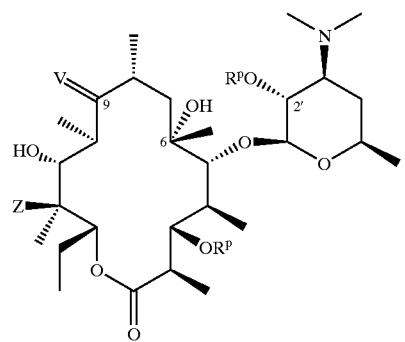

wherein Z is hydroxyl or protected hydroxyl group;

(c) treating the compound from step (b) with an alkylating agent having the formula:

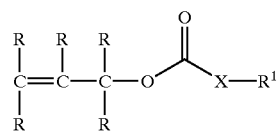

wherein R is as defined above;
$R^1$ is an alkyl group of one to ten carbon atoms, and
X is O or NR', wherein R' is an alkyl or an aryl; or $R^1$ and R' taken together form an aromatic or non-aromatic ring; in the presence of palladium catalyst and a phosphine to obtain a compound of the formula:

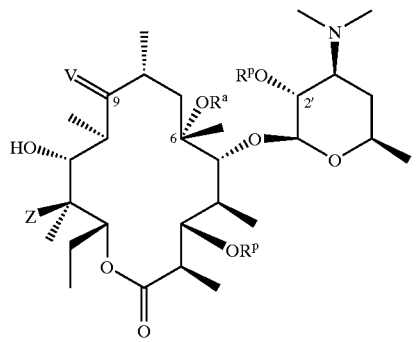

(d) deprotecting and deoximating the compound from step (c) to obtain a compound of formula:

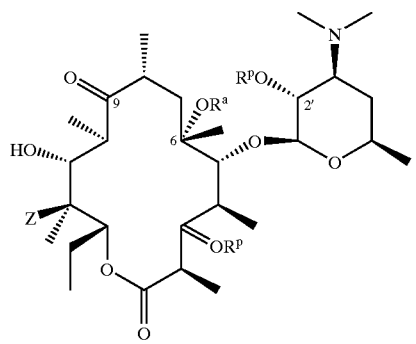

(e) optionally protecting the 2'- and 3- hydroxyl groups and reacting the compound from step (d) with 1,1'-carbonyldiimidazole, in the presence of an amine base or an amine base catalyst followed by reaction with ammonium hydroxide optionally carried out in the presence of a strong base to obtain a compound having the formula:

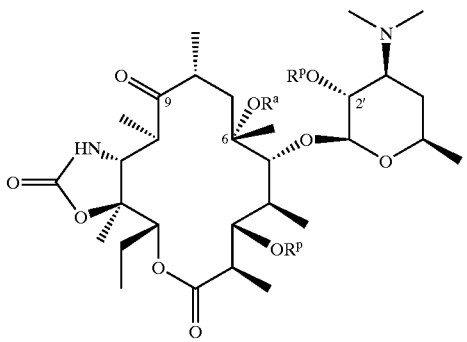

(f) optionally deprotecting the 3-hydroxyl group and oxidizing the 3-hydroxyl group; and (g) optionally deprotecting the hydroxyl-protecting groups.

26. The process according to claim 25, wherein $R^p$ is independently selected at each occurrence from the group consisting of acetyl, benzoyl, and trimethylsilyl.

27. The process according to claim 25, wherein V is

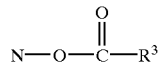

and $R^3$ is phenyl, and wherein $R^p$ is benzoyl.

28. The process according to claim 25, wherein V is N—O—$R^2$, wherein $R^2$ and $R^p$ at each occurrence are trimethylsilyl.

29. The process according to claim 25, wherein $R^p$ is acetyl at the 2'- and trimethylsilyl at the 4"-position.

30. The process according to claim 25, wherein V in the erythromycin derivative of step (a) has the formula:

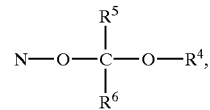

wherein $R^5$ and $R^6$ taken together with the carbon to which they are attached form a cyclohexyl ring and $R^4$ is isopropyl.

* * * * *

UNITED STATES PATENT AND TRADEMARK OFFICE
CERTIFICATE OF CORRECTION

PATENT NO. : 6,437,106 B1
DATED : August 20, 2002
INVENTOR(S) : Eric J. Stoner et al.

Page 1 of 1

It is certified that error appears in the above-identified patent and that said Letters Patent is hereby corrected as shown below:

Column 48,
Line 15, Formula 7g replace 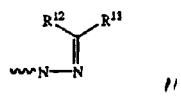

insert 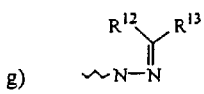

Column 51,
Line 40, Formula 9f replace 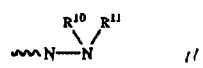

insert 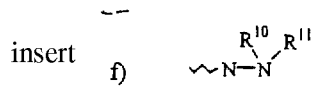

Line 51, Formula 9g replace 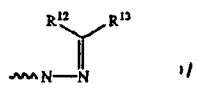

insert 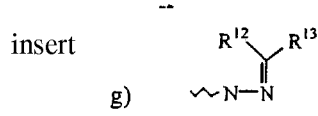

Column 54,
Line 30, Formula 25d replace

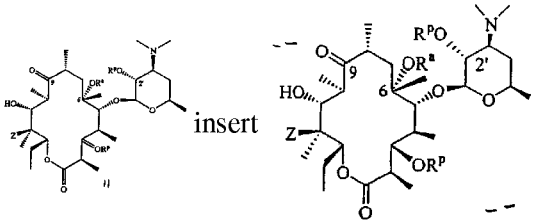 insert

Signed and Sealed this

Ninth Day of September, 2003

JAMES E. ROGAN
*Director of the United States Patent and Trademark Office*